United States Patent
Clark et al.

(10) Patent No.: US 9,766,249 B2
(45) Date of Patent: *Sep. 19, 2017

(54) COMPOSITIONS AND METHODS FOR PREDICTION OF DRUG SENSITIVITY, RESISTANCE, AND DISEASE PROGRESSION

(75) Inventors: Douglas P. Clark, Baltimore, MD (US); Adam Schayowitz, Bethesda, MD (US); Cirilo D. Cabradilla, Gaithersburg, MD (US)

(73) Assignee: BioMarker Strategies, LLC, Rockville, MD (US)

( * ) Notice: Subject to any disclaimer, the term of this patent is extended or adjusted under 35 U.S.C. 154(b) by 235 days.

This patent is subject to a terminal disclaimer.

(21) Appl. No.: 13/089,219

(22) Filed: Apr. 18, 2011

(65) Prior Publication Data
US 2012/0094853 A1    Apr. 19, 2012

Related U.S. Application Data

(60) Provisional application No. 61/325,717, filed on Apr. 19, 2010, provisional application No. 61/356,495, filed on Jun. 18, 2010, provisional application No. 61/421,178, filed on Dec. 8, 2010, provisional application No. 61/443,146, filed on Feb. 15, 2011.

(51) Int. Cl.
| | |
|---|---|
| *C40B 30/04* | (2006.01) |
| *G01N 33/68* | (2006.01) |
| *G01N 33/50* | (2006.01) |
| *C12Q 1/02* | (2006.01) |
| *C12Q 1/68* | (2006.01) |
| *C12Q 1/70* | (2006.01) |
| *G06F 19/12* | (2011.01) |
| *G06F 19/18* | (2011.01) |

(52) U.S. Cl.
CPC ..... *G01N 33/6842* (2013.01); *G01N 33/5041* (2013.01); *G01N 2800/52* (2013.01); *G06F 19/12* (2013.01); *G06F 19/18* (2013.01)

(58) Field of Classification Search
USPC ................. 435/6.1, 6.12, 6.13, 7.1
See application file for complete search history.

(56) References Cited

U.S. PATENT DOCUMENTS

| | | | |
|---|---|---|---|
| 6,218,122 B1 | 4/2001 | Friend et al. | |
| 2008/0293069 A1* | 11/2008 | Kulesza et al. | 435/6 |
| 2009/0162853 A1 | 6/2009 | Clark et al. | |

FOREIGN PATENT DOCUMENTS

| | | |
|---|---|---|
| CA | 2703631 A1 | 4/2009 |
| WO | WO 2006/121510 A2 | 11/2006 |
| WO | WO 2006/133399 A1 | 12/2006 |
| WO | WO 2007/028005 A2 | 3/2007 |
| WO | WO 2007/143183 A2 | 12/2007 |

OTHER PUBLICATIONS

Mx3000P; Mx3000PTM Real-Time PCR System Instruction Manual Software version 2.0; Stratagene; p. 1 (2004).*
R&D Systems; Methods for Detecting Protein Phosphorylation; http://www.rndsystems.com/mini_review_detail_objectname_MR08_ProteinPhosphorylation.aspx; pp. 1-6, available Apr. 20, 2008.*
Huarte et al., "PILAR is a novel modulator of human T-cell expansion", Blood, 112(4):1259-68 (2008).
Hartz et al., "17-β-Estradiol: a powerful modulator of blood-brain barrier BCRP activity", J. Cereb. Blood Flow Metab., 30(10):1742-55 (2010).
Jimeno et al., "Evaluation of the novel mitotic modulator ON 01910.Na in pancreatic cancer and preclinical development of an ex vivo predictive assay", Oncogene, 28(4):610-8 (2009). Epub Nov. 24, 2008.
International Search Report (ISR) from PCT/US2011/032935.
Clark P. Douglas: "Ex vivo biomarkers: functional tools to guide targeted drug development and therapy", Expert Review of Molecular Diagnostics, vol. 9, No. 8, Nov. 1, 2009, pp. 787-794, XP055076099.

(Continued)

*Primary Examiner* — Antonio Galisteo Gonzalez
(74) *Attorney, Agent, or Firm* — DLA Piper LLP (US)

(57) ABSTRACT

The present invention is based on the discovery that functional stratification and/or signaling profiles can be used for diagnosing disease status, determining drug resistance or sensitivity of cancer cells, monitoring a disease or responsiveness to a therapeutic agent, and/or predicting a therapeutic outcome for a subject. Provided herein are assays for diagnosis and/or prognosis of diseases in patients. Also provided are compositions and methods that evaluate the resistance or sensitivity of diseases to targeted therapeutic agents prior to initiation of the therapeutic regimen and to monitor the therapeutic effects of the therapeutic regimen. Also provided are methods for determining the difference between a basal level or state of a molecule in a sample and the level or state of the molecule after stimulation of a portion of the live sample with a modulator ex vivo, wherein the difference is expressed as a value which is indicative of the presence, absence or risk of having a disease. The methods of the invention may also be used for predicting the effect of an agent on the disease and monitoring the course of a subject's therapy.

8 Claims, 26 Drawing Sheets

(56) References Cited

OTHER PUBLICATIONS

Clark et al: "SP165 Optimizing information obtained from fine needle aspiration (FNA) biopsies", European Journal of Cancer. Supplement, Pergamon, Oxford, GB, vol. 7, No. 4, Oct. 1, 2009 p. 2, XP026692127, ISSN: 1359-6349, DOI: 10.101651359-6349(09)72109-3.
Lavallie E R et al: "Use of ex vivo systems for biomarker discovery", Current Opinion in Pharmacology, Elsevier Science Publishers, NL, vol. 8, No. 5, Oct. 1, 2008, pp. 647-653, XP025609346, ISSN: 1471-4892, DOI: 10.1016/J.COPH.2008.08.003.
A Jimeno et al: "Evaluation of the novel mitotic modulator ON 01910.Na in pancreatic cancer and preclinical development of an ex vivo predictive assay", ONCOGENE, vol. 28, No. 4, Nov. 24, 2008, pp. 610-618, XP055076292, ISSN:0950-9232, DOI: 10.1038/onc.2008.424.
Adam Schayowitz et al: "Functional Profiling of Live Melanoma Samples Using a Novel Automated Platform", PLos One, vol. 7, No. 12, Dec. 28, 2012, p. e52760, XP055076247, DOI: 10.1371/journal.pone.0052760.
Adam Schayowitz et al: "Functional Stratification of Breast Carcinoma Cells Enables Predictive Therapeutic Strategies", Apr. 5, 2011, XP055076106, Retrieved from the Internet: URL:http://www.biomarkerstrategies.com/PR/AACR2011 Poster FINAL.pdf.
Search Report regarding European Application No. 11 77 2505.
Farrington, D. L. et al.: "*Development and validation of a phosphorylated SMAD ex vivo stimulation assay*"; Biomarkers, vol. 12, No. 3; May 2007, pp. 313-330.
Japanese Office Action issued on Oct. 14, 2015, regarding JP 2013-506214.
Chinese Office Action issued on Mar. 18, 2016, regarding CN 201180030332.9.
Canadian Office Action issued on Mar. 9, 2017, regarding CA 2,795,362.

* cited by examiner

Baseline

| | MDA | MCP-7 | HCC | SKBR-3 | BT-474 |
|---|---|---|---|---|---|
| EGFR | Low | | Low | Low | Low |
| HER2 | Low | | | High | High |
| HER3 | | Low | High | High | High |
| AKT-Ser | Low | Low | Low | Low | Low |
| AKT-Thr | High | High | High | High | High |
| ERK | Low | Low | Low | Low | Low |
| Src | Low | Low | Low | Low | Low |
| Stat1 | Low | Low | Low | Low | Low |
| Stat3 | High | High | High | Low | Low |
| Trk | Low | Low | Low | Low | Low |
| Ret | | | | | |
| Lck | Low | Low | Low | Low | |
| Met | | | Low | | |
| Ron | | | | | |

| | |
|---|---|
| High | |
| Medium | |
| Low | |
| | No Response |

Figure 2A

EGF Stimulated

| | MDA | MCF-7 | HCC | SKBR-3 | BT-474 |
|---|---|---|---|---|---|
| EGFR | High | High | | High | Low |
| HER2 | | High | | | High |
| HER3 | | Low | | Low | High |
| AKT-Ser | High | High | High | High | High |
| AKT-Thr | High | High | | High | High |
| ERK | Low | High | High | High | High |
| Src | | Low | | | |
| Stat1 | | | Low | High | |
| Stat3 | | | High | High | |
| Trk | | High | | | |
| Ret | | High | | | |
| Lck | Low | Low | High | | |
| Met | | High | | | |
| Ron | | | Low | | |

| | |
|---|---|
| High= 1+ Fold Induction | |
| Medium= 0.5-1.0 Fold Induction | |
| Low=0.2-0.49 Fold Induction | |
| No Response= 0-0.19 | |

Figure 2B

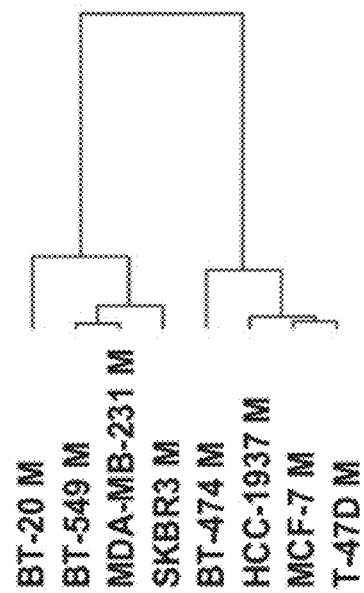
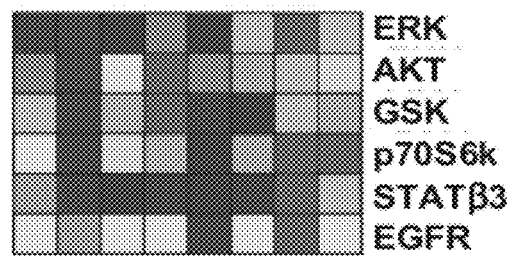
Figure 7

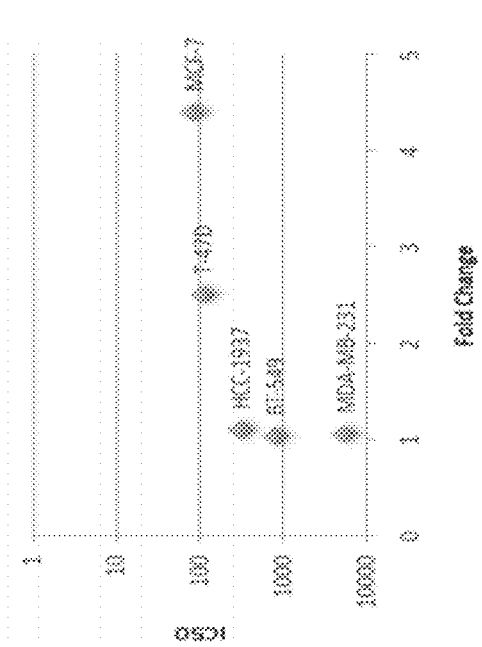
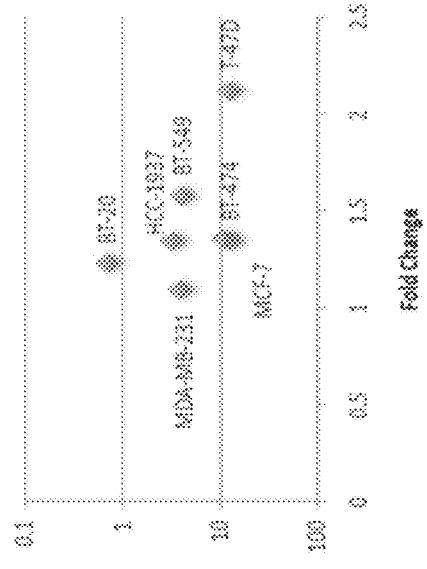
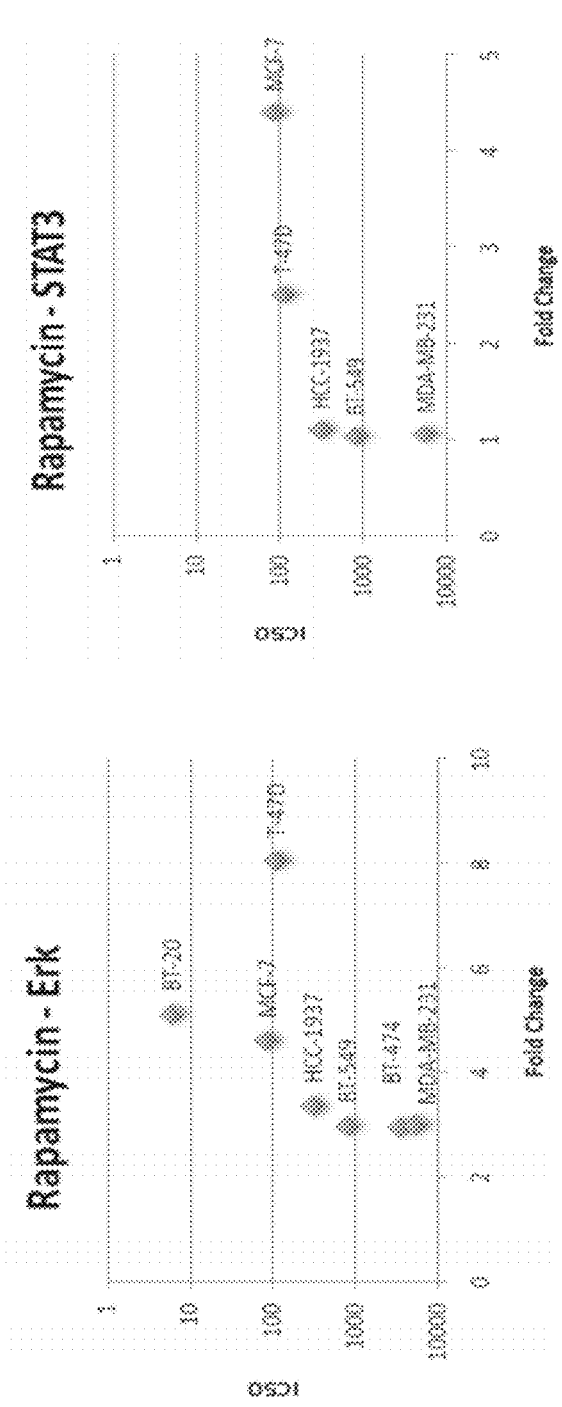
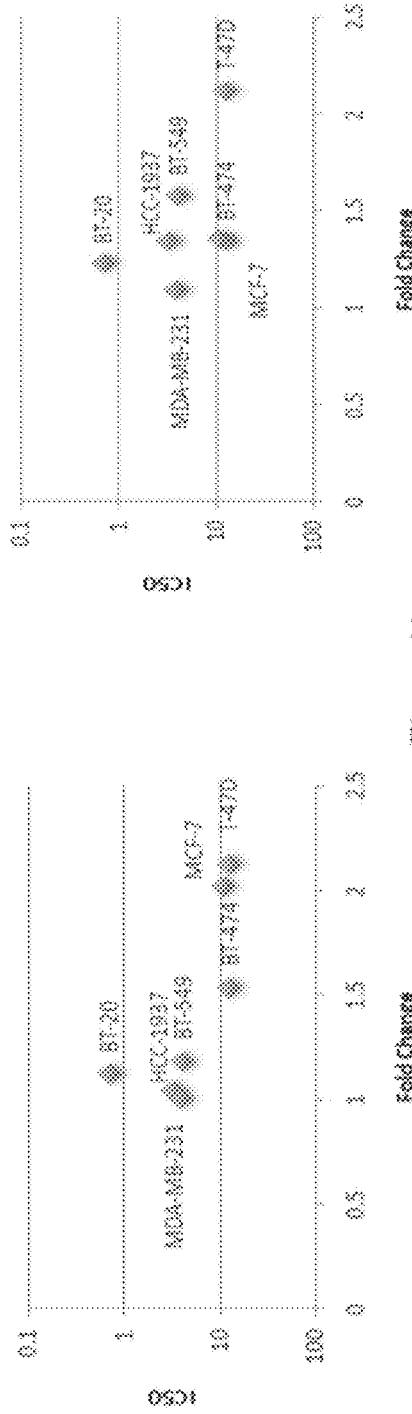
Figure 11

COMPOSITIONS AND METHODS FOR PREDICTION OF DRUG SENSITIVITY, RESISTANCE, AND DISEASE PROGRESSION

CROSS REFERENCE TO RELATED APPLICATIONS

This application claims the benefit of priority under 35 U.S.C. §119(e) of U.S. Ser. Nos. 61/325,717 filed Apr. 19, 2010, 61/356,495 filed Jun. 18, 2010, 61/421,178 filed Dec. 8, 2010, and 61/443,146 filed Feb. 15, 2011, the entire contents of which are incorporated herein by reference.

BACKGROUND OF THE INVENTION

Field of the Invention

The invention relates generally to the prediction of drug response and monitoring a disease state in a subject and more specifically to functional stratification of and signaling profiles of cancer cells upon modulation.

Background Information

Traditional pathological samples have been largely processed using methods that involve killing the cells using processing techniques that compromise the biological integrity of the sample. Such methods are generally performed in a laboratory well away from the point of care. These traditional methods do not permit the examination of live cells, including dynamic, live-cell related biomarkers, and do not allow for rapid sample processing or analytical result generation at or near the point of care. This lack of complete and rapidly obtained information can prevent doctors from identifying the proper treatment regimen or at the least slow the process which adversely affects the patient's quality of life.

For example, oncologists have a growing number of treatment options available to them, including different combinations of drugs that are characterized as standard of care, and a number of drugs that do not carry a label claim for a particular cancer, but for which there is evidence of efficacy in that cancer. The best likelihood of good treatment outcome requires that patients be assigned to optimal available cancer treatment, and that this assignment be made as quickly as possible following diagnosis.

While some cancers are beginning to be subclassified and treated using genomic markers, reliable genomic markers are not available for all cancers, which may be better characterized as exhibiting abnormal expression of one or (typically) many normal genes. Currently available biomarker tests to diagnose particular types of cancer and evaluate the likely effectiveness of different treatment strategies based on gene expression may have one or more disadvantages, for example: (1) the tests may be designed for testing blood and are not readily adapted for testing solid tumors; (2) sample preparation methods for solid tumor samples, may be unsuitable for handling live cells or performing subsequent measurements of marker expression; (3) small samples, e.g., obtained using fine needle biopsies, may not provide sufficient tissue for complete analysis; (4) the tests may require in vitro culturing of the cells, extended incubation periods, and/or significant delays between the time that the test cells are obtained from the patient and the time the cells are tested, resulting potential for wide variation and external influences on marker expression; (5) the tests may be unsuited for measuring expression of a multiplicity of genes, phosphoproteins or other markers in parallel, which may be critical for recognizing and characterizing the expression as abnormal; (6) the tests may be non-quantitative, relying principally on immunohistochemistry to determine the presence or absence of a protein as opposed to relative levels of expression of genes; (7) the reagents and cell handling conditions are not strictly controlled, leading to a high degree of variability from test to test and lab to lab; (8) the tests may be unsuited to analyzing nucleic acid levels, due to the instability of nucleic acid molecules and the practical difficulty of obtaining sufficiently fresh samples from the patients; and (9) the tests may involve fixing of the cells before any gene expression analysis can be performed, e.g., in the presence or absence of selected reagents.

Recently, several groups have published studies concerning the classification of various cancer types by microarray gene expression analysis (see, e.g. Golub et al., *Science* 286:531-537 (1999); Bhattacharjae et al., *Proc. Nat. Acad. Sci. USA* 98:13790-13795 (2001); Chen-Hsiang et al., *Bioinformatics* 17 (Suppl. 1): S316-S322 (2001); Ramaswamy et al., *Proc. Natl. Acad. Sci. USA* 98:1514915154 (2001)). Certain classifications of human breast cancers based on gene expression patterns have also been reported (Martin et al., Cancer Res. 60:2232-2238 (2000); West et al., *Proc. Natl. Acad. Sci. USA* 98:11462-11467 (2001); Sorlie et al., *Proc. Natl. Acad. Sci. USA* 98:1086910874 (2001); Yan et al., *Cancer Res.* 61:8375-8380 (2001)). However, these studies mostly focus on improving and refining the already established classification of various types of cancer, including breast cancer, and generally do not provide new insights into the relationships of the differentially expressed genes or functional cellular information. These studies do not link the findings to treatment strategies in order to improve the clinical outcome of cancer therapy, and they do not address the problem of improving and standardizing existing techniques of cell handling and analysis.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has been insufficient for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug HERCEPTIN®. (Genentech, Inc., South San Francisco, Calif.). For most cancers, however, the pathologies in gene expression may be subtler and may involve patterns of expression of multiple genes or expression of genes in response to particular stimuli.

A tumor cell's response to a targeted therapeutic drug is dependent not only on the presence of the target, but also to the multitude of molecules, and their variants, within the signaling network. The term "ex vivo biomarker" defines a novel class of biomarkers—those which are evoked by live tumor cells after they have been removed from the patient. In the context of molecular biomarkers this refers to the process of removing viable cells from a patient through peripheral blood or bone marrow collection, during surgery, circulating tumor cells, or through a minimally-invasive biopsy such as a fine needle aspiration biopsy (FNA). The viable sample is then stimulated in vitro. In oncology applications these stimuli may be growth factors, such as epidermal growth factor, that are relevant to the signal transduction networks targeted by new therapeutic drugs. The biomarkers themselves can represent any dynamic biomolecule, but may be newly modified phosphoproteins or newly expressed mRNAs in the signaling network. Cellular events occurring rapidly (minutes) after ex vivo stimulation, such as protein phosphorylation events, may be considered "proximal" to the stimulus and may be most valuable in determining the dominant signal transduction pathways utilized by the tumor. Events occurring later following ex vivo stimulation (minutes to hours), such as new mRNA transcription, may be considered "distal" markers and may be more useful in assessing a composite view of the signal transduction events and their impact on cellular functions such as proliferation or apoptosis. Multiplexed panels of such phosphoproteins, or gene expression microarrays, may facilitate the generation of comprehensive functional profiles that are distinct from, and more informative than profiles generated from fixed tissues. In some cases the effect of a molecularly targeted agent (MTA) on the pathway could be monitored ex vivo by stimulating the sample in the presence of a modulator, such as a chemical pathway inhibitor or the MTA itself. Overall, ex vivo biomarkers offer the possibility of functional assays that interrogate entire signal transduction networks. Such assays offer several possible applications, including patient stratification based on functional information to inform clinical trial design or clinical management and novel pharmacodynamic assays for use in the development of targeted therapies. (Clark D P. Ex vivo biomarkers: functional tools to guide targeted drug development and therapy. *Expert Rev Mol Diagn* 2009; 9(8):787-94).

Thus, there remains a need to develop improved compositions and methods for diagnosing disease status and determining drug sensitivity of cancer cells based on functional stratification and/or signaling profiles.

SUMMARY OF THE INVENTION

The present invention is based on the discovery that functional stratification and/or signaling profiles can be used for diagnosing or prognosing disease status, determining drug resistance or sensitivity of cancer cells, monitoring a disease or responsiveness to a therapeutic agent, and/or predicting a therapeutic outcome for a subject. Provided herein are assays for diagnosis and/or prognosis of diseases in patients. Also provided are compositions and methods that evaluate the resistance or sensitivity of diseases to targeted therapeutic agents prior to initiation of the therapeutic regimen and to monitor the therapeutic effects of the therapeutic regimen.

Thus, in one aspect, the invention provides a method for the diagnosis of a disease in a subject. The method includes determining the difference between a basal level or state of a molecule in a sample and the level or state of the molecule after contacting a portion of the sample with a modulator ex vivo, wherein the difference is expressed as a value which is indicative of the presence, absence or risk of having a disease. Preferably the sample contains viable (live) cells. In one embodiment, the molecule is a protein or nucleic acid molecule. In another embodiment, the molecule includes a protein, nucleic acid, lipid, sugar, carbohydrate, or metabolite molecule. In one embodiment, the protein is modified by post-translational modification. In another embodiment, the post-translational modification is selected from the group consisting of phosphorylation, acetylation, amidation, methylation, nitrosylation, fatty acid addition, lipid addition, glycosylation, and ubiquitination.

In one embodiment, the tumor sample is from a solid tumor. In another embodiment, the tumor sample is obtained by fine needle aspiration, core biopsy, circulating tumor cells, or surgically excised tissue sample. In another embodiment, the method further includes exposing the sample to a therapeutic agent or a combination thereof. In yet another embodiment, the step of determining the difference between a basal level or state of a molecule in the sample is performed with a computer. In yet another embodiment, the molecule is analyzed using a method selected from the group consisting of an array, ELISA, bioplex, luminex, LC-mass spectrometry, flow cytometry, RIA, Northern blot, Southern blot, Western blot, and PCR.

In another aspect, the invention provides a method for the prognosis of a disease in a subject. The method includes determining the difference between a basal level or state of a molecule in a sample and the level or state of the molecule after contacting a portion of the sample with a modulator ex vivo; wherein the difference in the basal level or state of the molecule expressed as a value is indicative of the prognosis. In one embodiment, the molecule is a protein or nucleic acid molecule. In another embodiment, the molecule includes a protein, nucleic acid, lipid, sugar, carbohydrate, or metabolite molecule. In one embodiment, the protein is modified by post-translational modification. In another embodiment, the post-translational modification is selected from the group consisting of phosphorylation, acetylation, amidation, methylation, nitrosylation, fatty acid addition, lipid addition, glycosylation, and ubiquitination.

In one embodiment, the tumor sample is from a solid tumor. In another embodiment, the tumor sample is obtained by fine needle aspiration, core biopsy, circulating tumor cells, or surgically excised tissue sample. In another embodiment, the method further includes exposing the sample to a therapeutic agent or a combination thereof. In yet another embodiment, the step of determining the difference between a basal level or state of a molecule in the sample is performed with a computer. In yet another embodiment, the molecule is analyzed using a method selected from the group consisting of an array, ELISA, multiplex, bioplex, luminex, mass spectrometry, flow cytometry, Northern blot, Southern blot, Western blot, PCR and RIA.

In another aspect, the invention provides a method for predicting the effect of an agent or combination of agents. The method includes determining the difference between a basal level or state of a molecule in a sample and the level or state of the molecule after contacting a portion of the sample with a modulator ex vivo, wherein the difference in the basal level or state of the molecule expressed as a value is indicative of a positive or negative effect of the agent. In one embodiment, the molecule is a protein or nucleic acid molecule. In another embodiment, the molecule includes a protein, nucleic acid, lipid, sugar, carbohydrate, or metabolite molecule. In another embodiment, the agent interacts directly with the molecule in the sample. In another embodiment, the effect is the activation or inhibition of a cellular pathway selected from the group consisting of a metabolic pathway, a replication pathway, a cellular signaling pathway, an oncogenic signaling pathway, an apoptotic pathway, and a pro-angiogenic pathway. In yet another embodiment, the step of determining the difference between a basal level or state of a molecule in the sample is performed with a computer. In yet another embodiment, the molecule is analyzed using a method selected from the group consisting of an array, ELISA, multiplex, bioplex, luminex, mass spectrometry, flow cytometry, Northern blot, Southern blot, Western blot, PCR and RIA.

In another aspect, the invention provides a method of monitoring a disease or responsiveness to a therapeutic agent, therapeutic regimen, or course of therapy for a subject. The method includes determining the difference between a basal level or state of a molecule in a sample and the level or state of the molecule after contacting a portion of the sample with a modulator ex vivo, optionally prior to, simultaneously with or following the therapeutic agent, therapeutic regimen, or course of therapy; wherein the difference in the basal level or state of the molecule expressed as a value is indicative of a positive or negative treatment.

In another aspect, the invention provides a method of monitoring a disease or course of therapy for a subject. The method includes determining the difference between a basal level or state of a molecule in a sample and the level or state of the molecule after contacting a portion of the sample with a modulator ex vivo, optionally prior to, simultaneously with or following the course of therapy; wherein the difference in the basal level or state of the molecule expressed as a value is indicative of a positive or negative treatment. In one embodiment, the molecule is a protein or nucleic acid molecule. In another embodiment, the molecule includes a protein, nucleic acid, lipid, sugar, carbohydrate, or metabolite molecule. In another embodiment, a positive treatment is indicative of the subject being a responder to the course of therapy. In another embodiment, a negative treatment is indicative of the subject having resistance to the course of therapy. In yet another embodiment, the step of determining the difference between a basal level or state of a molecule in the sample is performed with a computer. In yet another embodiment, the molecule is analyzed using a method selected from the group consisting of an array, ELISA, multiplex, bioplex, luminex, mass spectrometry, flow cytometry, Northern blot, Southern blot, Western blot, PCR and RIA.

In another aspect, the invention provides a method of screening test agents for an effect on a molecule. The method includes contacting a sample containing the molecule or molecules with the test agent ex vivo, then determining a difference between a basal level or state of the molecule in the sample and the level or state of the molecule after contacting a portion of the sample with a modulator ex vivo; wherein a difference in the basal level or state of the molecule before and after contacting with the test agent is indicative of an effect on the molecule. In one embodiment, functional signaling circuitry is assessed to predict the effect of two test agents in combination. In another embodiment, the sample is selected from the group consisting of tissue, blood, ascites, saliva, urine, perspiration, tears, semen, serum, plasma, amniotic fluid, pleural fluid, cerebrospinal fluid, a cell line, a xenograft, a tumor, pericardial fluid, and combinations thereof.

In one embodiment, the molecule is a protein or nucleic acid molecule. In another embodiment, the molecule includes a protein, nucleic acid, lipid, sugar, carbohydrate, or metabolite molecule. In another embodiment, the molecule activates or inhibits a cellular pathway selected from the group consisting of a metabolic pathway, a replication pathway, a cellular signaling pathway, an oncogenic signaling pathway, an apoptotic pathway, and a pro-angiogenic pathway. Exemplary test agents include, but are not limited to, a small molecule chemical, a chemotherapeutic agent, a hormone, a protein, a peptide, a peptidomimetic, a protein, an antibody, a nucleic acid, an RNAi molecule, and an antisense molecule. In yet another embodiment, the step of determining the difference between a basal level or state of a molecule in the sample is performed with a computer. In yet another embodiment, the molecule is analyzed using a method selected from the group consisting of an array, ELISA, multiplex, bioplex, luminex, mass spectrometry, flow cytometry, Northern blot, Southern blot, Western blot, PCR and RIA.

In another aspect, the invention provides a method for stratification of patients based on responsiveness to a therapeutic agent or therapeutic regimen. The method includes determining the difference between a basal level or state of a molecule in a sample from a subject and the level or state of the molecule after contacting a portion of the sample with a modulator ex vivo; wherein the difference in the basal level or state of the molecule expressed as a value is indicative of a positive or negative response to a therapeutic agent or therapeutic regimen. In one embodiment, the molecule is a protein or nucleic acid molecule. In another embodiment, the molecule includes a protein, nucleic acid, lipid, sugar, carbohydrate, or metabolite molecule. In another embodiment, a positive response is indicative of the subject being a responder to the therapeutic agent or therapeutic regimen. In another embodiment, a negative response is indicative of the subject having resistance to the therapeutic agent or therapeutic regimen. Exemplary test agents include, but are not limited to, a small molecule chemical, a chemotherapeutic agent, a hormone, a protein, a peptide, a peptidomimetic, a protein, an antibody, a nucleic acid, an RNAi molecule, and an antisense molecule. In yet another embodiment, the step of determining the difference between a basal level or state of a molecule in the sample is performed with a computer. In yet another embodiment, the molecule is analyzed using a method selected from the group consisting of an array, ELISA, multiplex, bioplex, luminex, mass spectrometry, flow cytometry, Northern blot, Southern blot, Western blot, PCR and RIA.

In another aspect, the invention provides a method of determining drug resistance or sensitivity in a subject. The method includes comparing the basal level or state of a molecule in a sample from a subject with the level or state of the molecule after ex vivo inhibition in the absence of a stimulatory compound. In one embodiment, the molecule is a protein or nucleic acid molecule. In another embodiment, the molecule includes a protein, nucleic acid, lipid, sugar, carbohydrate, or metabolite molecule.

In various aspects, the sample is selected from the group consisting of tissue, blood, ascites, saliva, urine, perspiration, tears, semen, serum, plasma, amniotic fluid, pleural fluid, cerebrospinal fluid, a cell line, a xenograft, a tumor, pericardial fluid, and combinations thereof. In various aspects, the tumor sample is from a solid tumor. In various aspects, the tumor sample can include cancer selected from the group consisting of colorectal, esophageal, stomach, lung, prostate, uterine, breast, skin, endocrine, urinary, pancreas, ovarian, cervical, head and neck, liver, bone, biliary tract, small intestine, hematopoietic, vaginal, testicular, anal, kidney, brain, eye cancer, leukemia, lymphoma, soft tissue, melanoma, and metastases thereof.

Exemplary diseases include, but are not limited to, stroke, cardiovascular disease, chronic obstructive pulmonary disorder, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), cancer, pathogen-mediated disease, pleural effusions, rheumatoid arthritis, diabetic retinopathy, retinitis pigmentosa, and retinopathies, including diabetic retinopathy and retinopathy of prematurity, inflammatory diseases, restenosis, edema (including edema associated with pathologic situations such as cancers and edema induced by medical interventions such as chemotherapy), asthma, acute or adult respiratory distress syndrome (ARDS), lupus, vascular leakage, transplant (such as organ transplant, acute transplant or heterograft or homograft (such as is employed in burn treatment)) rejection; protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kinases such as Src-family kinases are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemic and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener's granulomatosis, and Behcet's disease; scleroderma; preeclampsia; thalassemia; Kaposi's sarcoma; and von Hippel Lindau disease.

In various aspects, the pathogen is selected from the group consisting of bacteria, fungi, viruses, spirochetes, and parasites. In various aspects, the virus is selected from the group consisting of Herpes simplex virus 1 (HSV1), Herpes simplex virus 2 (HSV2), respiratory syncytial virus, measles virus (MV), human cytomegalovirus (HCMV), vaccinia virus, human immunodeficiency virus type 1 (HIV-1), and hepatitis C virus (HCV).

In various embodiments, the modulator includes a stimulator or inhibitor. In various embodiments, the modulator is selected from a physical, biological or a chemical modulator. In various embodiments, the physical or chemical modulator includes a temperature change, density change, pH change, or color change. In various embodiments, the modulator includes epidermal growth factor (EGF), tissue plasminogen activator (TPA), other growth factors, or a combination thereof. In various embodiments, the at least one molecule includes a protein involved in a cellular pathway selected from the group consisting of a metabolic pathway, a replication pathway, a cellular signaling pathway, an oncogenic signaling pathway, an apoptotic pathway, and a pro-angiogenic pathway. In various embodiments, the at least one molecule includes a protein involved in RAS-RAF-MEK-ERK pathway. In various embodiments, the at least one molecule includes pErk1/2, pAKT, pP70S6k, pGSK3α/β, pmTOR, pSrc, pEGFR, pSTAT3, or combinations thereof.

In another aspect, the invention provides an ex vivo method for determining functional stratification of a live tumor sample of a subject. The method includes measuring at least one signal transduction phosphoprotein level for creating functional signaling profiles, ex vivo, in the absence of growth factor stimulation or in the absence of growth hormone stimulation, and, in the presence of an inhibitor and in the absence of the inhibitor. In one embodiment, the method includes measuring at least one signal transduction phosphoprotein level for creating functional signaling profiles, ex vivo, in response to a growth factor stimulation, in the presence of a MEK inhibitor and in the absence of the MEK inhibitor. In one embodiment, the inhibitor includes a MEK inhibitor, mTOR inhibitor, BRAF inhibitor, or combinations thereof. In one embodiment, the live tumor sample includes breast cancer cells, melanoma cells, or pancreatic cancer cells. In another embodiment, the phosphoprotein includes p-Erk 1/2, p-AKT, p-EGFR, p-Stat3, pP70S6K, pmTOR, pSrc, and/or pGSK3α/β. In another embodiment, the phosphoprotein is selected from the group consisting of p-Erk 1/2, p-AKT, p-EGFR, p-Stat3, pP70S6K, pmTOR, pSrc, pGSK3α/β, or a combination thereof. In various embodiments, the phosphoprotein is selected from at least one of the group consisting of 4EBP1, 4EBP1 pS65, 53BP1, ACC S79, ACC1, AIB-1, AKT, AKT S473, AKT T308, AMPK, AMPK T172, Annexin, AR, Bak, BAX, Bcl-2, Bcl-X, Bcl-xL, Beclin, Bid, BIM, Cadherin-E, Cadherin-N, Cadherin-P, Caspase 3 Active, Caspase 7 cleaved Asp198, Catenin Beta, Caveolin1, CD31, CDC2, Chk1, Chk1 pSer345, Chk2 (1C12), Chk2 pThr68, cJun P-S73, Claudin7 CLDN7, Collagen VI, Cox-2, Cyclin B1, Cyclin D1, Cyclin E1, DJ-1, eEF2, eEF2K, EGFR, EGFR Y992, EGFR Y1173, eIF4E, ER-a S118, ERCC1, FAK, Fibronectin, FOX03a, FOX03a S318/321, Gata3, GSK3 S21/S9, GSK3-Beta, HER2 pY1248, IGFBP2, IGFR1b, INPP4B, IRS-1, Jnk2, Kit-c, K-RAS, Ku80, MAPK P-T202/204, MEK1, MEK1 pS217/221, MIG-6, Mre11 (31H4), MSH2, MSH6, Myc, NF-kB p65, NF2, Notch 1, Notch3, p21, p27, p27 pT157, p27 pT198, p38/MAPK, p38 T180/182, p53, p70S6K, p70S6K T389, p90 RSK P-T359/S363, PARP cleaved, Paxillin, PCNA, PDK1 P-S241, Pea15, Pea15 pS116, PI3K P110a, PI3K-p85, PKC 5657, PKCa, PR, Pras40 pT246, PTCH, PTEN, Rab25, Rad50, Rad51, Raf-A pS299, Raf-B, Raf-C, Raf-c pS388, Rb (4H1), Rb pS807/811, S6 S235/236, S6 S240/244, Shc pY317, Smad3, Snail, Src, Src P-Y527, Src Y416, Stat3 P-S705, Stat5, Stathmin, Tau, Taz, Taz P-Ser79, Telomerase, Transglutaminase, Tuberin/TSC2, Vasp, VEGFR2, Xiap, XRCC1, Y Box Binding Protein 1, YAP, YAP pS127, YB1 pS102, or a combination thereof. In one embodiment, at least two different groups of functional signaling profiles are identified. In another embodiment, at least four different groups of functional signaling profiles are identified. In one embodiment, the growth factor stimulation includes an Epidermal Growth Factor Receptor ligand. In an additional embodiment, the Epidermal Growth Factor Receptor ligand is Epidermal Growth Factor (EGF). In various embodiments, the growth factor includes Epidermal Growth Factor (EGF), insulin-like growth factor (IGF), platelet-derived growth factor (PDGF), fibroblast growth factor (FGF), melanocyte stimulating hormone, hepatocyte growth factor, vascular endothelial growth factor (VEGF), PTK7, Trk, Ros, MuSK, Met, Axl, Tie, Eph, Ret Ryk, DDR, Ros, LMR, ALK, STYK1, or a combination thereof.

In another aspect, the invention provides a method for classifying cancer cell model systems. The method includes (a) measuring at least one signal transduction phosphoprotein levels to a selected group of cancer cells; (b) contacting the cancer cells with at least one growth factor or at least one inhibitor; (c) measuring at least one signal transduction phosphoprotein levels after step (b); (d) calculating a modulation score based on measurements from step (a) and step (c); and (e) classifying the cancer cells based on the modulation score of step (d). In one embodiment, the method further includes the step of predicting drug resistance or sensitivity of a live tumor sample of a subject based on the classification of the live tumor sample.

In one embodiment, the cancer cells include breast cancer cells. In another embodiment, the cancer cells include breast cancer cells, melanoma cells, or pancreatic cancer cells. In another embodiment, the phosphoprotein includes p-Erk 1/2, p-AKT, p-EGFR, p-Stat3, pP70S6K, pmTOR, pSrc, and/or pGSK3α/β. In another embodiment, the phosphoprotein is selected from the group consisting of p-Erk 1/2, p-AKT, p-EGFR, p-Stat3, pP70S6K, pmTOR, pSrc, pGSK3α/β, or a combination thereof. In various embodiments, the phosphoprotein is selected from at least one of the group consisting of 4EBP1, 4EBP1 pS65, 53BP1, ACC S79, ACC1, AIB-1, AKT, AKT 5473, AKT T308, AMPK, AMPK T172, Annexin, AR, Bak, BAX, Bcl-2, Bcl-X, Bcl-xL, Beclin, Bid, BIM, Cadherin-E, Cadherin-N, Cadherin-P, Caspase 3 Active, Caspase 7 cleaved Asp198, Catenin Beta, Caveolin1, CD31, CDC2, Chk1, Chk1 pSer345, Chk2 (1C12), Chk2 pThr68, cJun P-S73, Claudin7 CLDN7, Collagen VI, Cox-2, Cyclin B1, Cyclin D1, Cyclin E1, DJ-1, eEF2, eEF2K, EGFR, EGFR Y992, EGFR Y1173, eIF4E, ER-a 5118, ERCC1, FAK, Fibronectin, FOX03a, FOX03a S318/321, Gata3, GSK3 S21/S9, GSK3-Beta, HER2 pY1248, IGFBP2, IGFR1b, INPP4B, IRS-1, Jnk2, Kit-c, K-RAS, Ku80, MAPK P-T202/204, MEK1, MEK1 pS217/221, MIG-6, Mre11(31H4), MSH2, MSH6, Myc, NF-kB p65, NF2, Notch 1, Notch3, p21, p27, p27 pT157, p27 pT198, p38/MAPK, p38 T180/182, p53, p70S6K, p70S6K T389, p90 RSK P-T359/S363, PARP cleaved, Paxillin, PCNA, PDK1 P-S241, Pea15, Pea15 pS116, PI3K P110a, PI3K-p85, PKC 5657, PKCa, PR, Pras40 pT246, PTCH, PTEN, Rab25, Rad50, Rad51, Raf-A pS299, Raf-B, Raf-C, Raf-c p5388, Rb (4H1), Rb pS807/811, S6 S235/236, S6 S240/244, Shc pY317, Smad3, Snail, Src, Src P-Y527, Src Y416, Stat3 P-S705, Stat5, Stathmin, Tau, Taz, Taz P-Ser79, Telomerase, Transglutaminase, Tuberin/TSC2, Vasp, VEGFR2, Xiap, XRCC1, Y Box Binding Protein 1, YAP, YAP pS127, YB1 pS102, or a combination thereof. In one embodiment, at least two different groups of cancer cell classifications are identified. In another embodiment, at least four different groups of cancer cell classifications are identified. In one embodiment, the growth factor stimulation includes an Epidermal Growth Factor Receptor ligand. In an additional embodiment, the Epidermal Growth Factor Receptor ligand is Epidermal Growth Factor (EGF). In various aspects, the growth factor includes Epidermal Growth Factor (EGF), insulin-like growth factor (IGF), platelet-derived growth factor (PDGF), fibroblast growth factor (FGF), melanocyte stimulating hormone, hepatocyte growth factor, vascular endothelial growth factor (VEGF), PTK7, Trk, Ros, MuSK, Met, Axl, Tie, Eph, Ret Ryk, DDR, Ros, LMR, ALK, STYK1, or a combination thereof.

In another aspect, the invention provides a method for predicting outcome of a therapeutic regimen in a subject. The method includes (a) measuring basal level of at least one molecule of at least one cell from a subject having a disease in need of therapy; (b) exposing the at least one cell to a modulator ex vivo; (c) measuring level of the at least one signal transduction protein after step (b); and (d) comparing the difference between levels measured in (a) and (b) to cells with known property for drug resistance or sensitivity, thereby predicting the outcome of the therapeutic regimen in the subject.

In another aspect, the invention provides a method for predicting drug resistance or sensitivity of cells. The method includes (a) measuring basal level of at least one molecule of at least one cell; (b) exposing the at least one cell to a modulator ex vivo; (c) measuring level of the at least one signal transduction protein after step (b); and (d) comparing the difference between levels measured in (a) and (b) to cells with known property for drug resistance or sensitivity, thereby predicting drug resistance or sensitivity of the at least one cell. In one embodiment, the cell includes a melanoma cell. In another embodiment, the drug includes a BRAF inhibitor. In another embodiment, the drug includes a MEK inhibitor, mTOR inhibitor, BRAF inhibitor, or combinations thereof.

In one embodiment, the at least one molecule includes a signal transduction protein. In another embodiment, the at least one cell includes a tumor sample from a subject and the levels measured in (a) and (b) are performed ex vivo. In various embodiments, the tumor sample is from a solid tumor. In an additional embodiment, the tumor sample includes cancer selected from the group consisting of colorectal, esophageal, stomach, lung, prostate, uterine, breast, skin, endocrine, urinary, pancreas, ovarian, cervical, head and neck, liver, bone, biliary tract, small intestine, hematopoietic, vaginal, testicular, anal, kidney, brain, eye cancer, leukemia, lymphoma, soft tissue, melanoma, and metastases thereof. In various embodiments, the tumor sample is obtained by fine needle aspiration, core biopsy, circulating tumor cells, or surgically excised tissue sample.

In one embodiment, the drug resistance includes BRAF inhibitor resistance. In another embodiment, the at least one cell includes a serine/threonine-protein kinase B-Raf (BRAF) mutation. In another embodiment, the at least one cell includes a BRAF mutation and Cancer Osaka thyroid oncogene (COT) amplification. In an additional embodiment, the BRAF mutation is V600E.

In various embodiments, the comparing step is performed with a computer. In various embodiments, the measurements are performed using an assay selected from the group consisting of an array, ELISA, multiplex, bioplex, luminex, mass spectrometry, flow cytometry, Northern blot, Southern blot, Western blot, PCR and RIA.

In another aspect, the invention provides a method for classifying melanoma cells. The method includes (a) measuring a first basal level of at least one molecule of at least one melanoma cell; (b) comparing the first basal level measured in (a) to a second basal level of the at least one molecule of melanoma cells with known classifications, thereby classifying the at least one melanoma cell. In one embodiment, the at least one melanoma cell includes a tumor sample from a subject and the first basal level is measured ex vivo. In various embodiments, the classifications include metastatic state. In various embodiments, the tumor sample is obtained by fine needle aspiration, core biopsy, circulating tumor cells, or surgically excised tissue sample.

In another aspect, the invention provides a method for classifying melanoma cells. The method includes (a) measuring basal level of at least one molecule of at least one melanoma cell; (b) exposing the at least one melanoma cell to a inhibitory test agent; (c) measuring level of the at least one molecule after step (b); and (d) comparing the difference between levels measured in (a) and (b) to melanoma cells with known classifications, thereby classifying the at least one melanoma cell. In one embodiment, the at least one melanoma cell includes a tumor sample from a subject and measurements are performed ex vivo. In one embodiment, the inhibitory test agent includes a MEK inhibitor, mTOR inhibitor, BRAF inhibitor, or combinations thereof. In another embodiment, the classifications include metastatic state. In various embodiments, the tumor sample is obtained by fine needle aspiration, core biopsy, circulating tumor cells, or surgically excised tissue sample.

In another aspect, the invention provides a method for identifying drug resistance mechanisms or oncogene bypass mechanisms of melanoma cells. The method includes (a) exposing at least one melanoma cell to a inhibitory test agent; (b) measuring reductions of a plural of molecules after exposure of (a), thereby identifying drug resistance mechanisms or oncogene bypass mechanisms.

In one embodiment, the at least one melanoma cell includes a tumor sample from a subject and measurement are performed ex vivo. In various embodiments, the tumor sample includes cancer selected from the group consisting of colorectal, esophageal, stomach, lung, prostate, uterine, breast, skin, endocrine, urinary, pancreas, ovarian, cervical, head and neck, liver, bone, biliary tract, small intestine, hematopoietic, vaginal, testicular, anal, kidney, brain, eye cancer, leukemia, lymphoma, soft tissue, melanoma, and metastases thereof. In various embodiments, the at least one molecule includes a protein involved in a cellular pathway selected from the group consisting of a metabolic pathway, a replication pathway, a cellular signaling pathway, an oncogenic signaling pathway, an apoptotic pathway, and a pro-angiogenic pathway. In various embodiments, the at least one molecule includes a protein involved in RAS-RAF-MEK-ERK pathway. In various embodiments, the at least one molecule includes pErk1/2, pAKT, pP70S6k, pGSK3α/β, pEGFR, pSTAT3, pmTOR, pSrc, or combinations thereof. In various embodiments, the tumor sample is obtained by fine needle aspiration, core biopsy, circulating tumor cells, or surgically excised tissue sample.

BRIEF DESCRIPTION OF THE DRAWINGS

FIGS. 2A and 2B are functional signaling profiles of baseline (FIG. 2A) and EGF stimulated (FIG. 2B) for a set of five breast cancer cell lines.

FIG. 7 shows an exemplary cell line hierarchal clustering based on functional stratification.

DETAILED DESCRIPTION OF THE INVENTION

Figure 1:
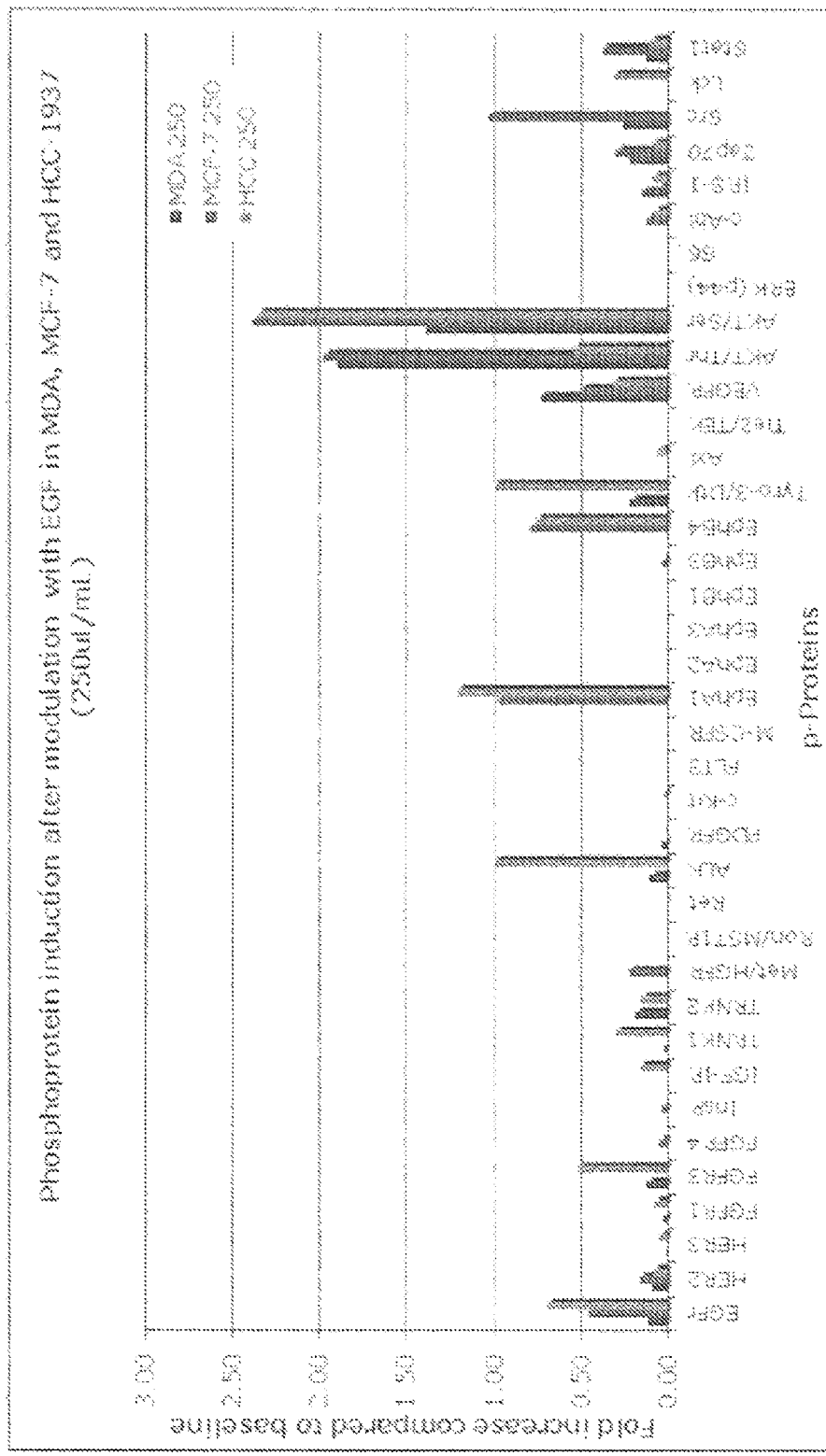
FIG. 1 is a graphical diagram summarizing data derived from a phosphoprotein array that contains 29 different phosphoproteins.

Before the present composition, methods, and treatment methodology are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described The invention provides a safe, effective, accurate, precise, reproducible, inexpensive, cost effective, efficient, fast and convenient method and "cartridge-based" system for collecting, handling and processing of cellular specimens ex vivo. These methods and cartridges can maintain viability of the samples during the process to maintain biomarker integrity, and optionally, evoking biomarkers such as phosphoproteins and nucleic acid molecules not present in original sample through ex vivo stimulation and/or inhibition. The invention provides fully integrated specimen and information management in a complete diagnostic cytology laboratory system and controlled conditions following biopsy, which minimizes variability between tests, minimizes the risk of biocontamination, and minimizes the effect of the sample preparation process itself on biomarker expression.

Embodiments of the present invention can be used to facilitate targeted treatment of diseases, and optionally also provide a tissue sample adequacy evaluation such as a cell-count, cell function and/or other connected analyses.

As one of skill in the art will appreciate, the devices, systems, kits and methods as described herein provide numerous advantages in a clinical or research setting. For example, they can be used to provide rapid, near patient, biopsy processing without the need to send the specimen to a remote laboratory. They can also be used to standardize and automate biopsy processing in a cost effective manner. The present invention can provide more detailed molecular information about the cells than current pathological processes allow which enables greater sub-classifications of cells in a biopsy (e.g., cancer or disease cells), optionally using new ex vivo biomarkers. Taken together, the advantages of the present invention allow for a rapid diagnosis near the point of care and the subsequent creation of more effective patient specific treatment regimens.

It should be understood that the methods of the invention may be performed alone or in conjunction with the systems and devices set forth in U.S. Publication No. 2009/0162853, incorporated herein by reference.

In one aspect, the invention provides molecular assays capable diagnosis and/or prognosis of a disease in a subject. In addition, the molecular assays of the invention are capable of both evaluating the sensitivity or resistance of a patient's disease to an agent prior to initiation of therapy and monitoring the therapy effects during treatment. The diagnostic assay directs therapy and determines prognosis of patients treated with targeted therapies.

Accordingly, the invention provides a method for the diagnosis and/or prognosis of disease in a subject. The method includes determining the difference between a basal level or state of a molecule in a sample and the level or state of the molecule after stimulation of a portion of the sample with a modulator ex vivo, wherein the difference is expressed as a value which is indicative of the presence, absence or risk of having a disease.

Exemplary modulators include, but are not limited to, physical, biological, or chemical modulators. Included in the term "modulators" are stimulators and inhibitors, such as small molecules (e.g. erlotinib, gefitinib, or lapatanib), and antibodies (e.g., HERCEPTIN®). In one embodiment, the modulator is an epidermal growth factor receptor (EGFR) inhibitor or activator. As used herein, the term "EGFR" refers to erbB gene family products. It will be understood by those skilled in the art that the EGFR may be a product of any erbB receptor encoded by any gene from the erbB gene family, and any homo- and heterodimers that these molecules are known to form. While erbB-1 product is the main receptor, the expression of which has been detected in previous studies, there is reason to believe that the cell lines and tumors tested herein also express other erbB gene family members. Lastly, the EGFR ligand or combination of ligand we used binds to almost all of the known EGFR receptor forms, and therefore our assay measures the effects exerted by those proteins. In another embodiment, the modulator is a combination of one or more modulators such as, for example, one or more of EGF, TGF-α, and Heregulin.

Thus, the quantitative or qualitative effect measured can be the expression level of a gene, such as, an immediate or delayed early gene family member. Suitable immediate or delayed early gene family members include, but are not limited to, FOS, JUN and DUSP 1-28.

As used herein, the term "disease" is used broadly to refer to any pathological condition of a part, organ, or system of a subject resulting from various causes, such as infection, genetic defect, or environmental stress, and characterized by an identifiable group of signs or symptoms. Exemplary diseases include, but are not limited to, stroke, cardiovascular disease, chronic obstructive pulmonary disorder, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), cancer, pathogen-mediated disease, pleural effusions, rheumatoid arthritis, diabetic retinopathy, retinitis pigmentosa, and retinopathies, including diabetic retinopathy and retinopathy of prematurity, inflammatory diseases, restenosis, edema (including edema associated with pathologic situations such as cancers and edema induced by medical interventions such as chemotherapy), asthma, acute or adult respiratory distress syndrome (ARDS), lupus, vascular leakage, transplant (such as organ transplant, acute transplant or heterograft or homograft (such as is employed in burn treatment)) rejection; protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kinases such as Src-family kinases are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculitides, including vasculitis, Kawasaki disease, thromboangiitis obliterans, Wegener's granulomatosis, and Behcet's disease; scleroderma; preeclampsia; thalassemia; Kaposi's sarcoma; and von Hippel Lindau disease.

In one embodiment, the disease is cancer. Exemplary cancers include, but are not limited to, colorectal, esophageal, stomach, lung, prostate, uterine, breast, skin, endocrine, urinary, pancreas, ovarian, cervical, head and neck, liver, bone, biliary tract, small intestine, hematopoietic, vaginal, testicular, anal, kidney, brain, eye cancer, leukemia, lymphoma, soft tissue, melanoma, and metastases thereof.

In another embodiment, the disease is a pathogen-mediated disease. Exemplary pathogens include, but are not limited to, bacteria, fungi, viruses, spirochetes, and parasites. Exemplary viruses include, but are not limited to, Herpes simplex virus 1 (HSV1), Herpes simplex virus 2 (HSV2), respiratory syncytial virus, measles virus (MV), human cytomegalovirus (HCMV), vaccinia virus, human immunodeficiency virus type 1 (HIV-1), and hepatitis C virus (HCV).

As used herein, the terms "sample" and "biological sample" refer to any sample suitable for the methods provided by the present invention. A sample of cells used in the present method can be obtained from tissue samples or bodily fluid from a subject, or tissue obtained by a biopsy procedure (e.g., a needle biopsy) or a surgical procedure. Thus, exemplary samples include, but are not limited to, a tissue sample, a frozen tissue sample, a biopsy specimen, a surgical specimen, a cytological specimen, a cell line, a xenograft, a tumor, a fine needle aspiration, whole blood, bone marrow, cerebral spinal fluid, peritoneal fluid, pleural fluid, lymph fluid, serum, plasma, amniotic fluid, mucus, plasma, urine, chyle, stool, sputum, perspiration, tears, semen, nipple aspirate, saliva, and any combination thereof. In certain embodiments, the sample can be a fraction of a blood sample such as a peripheral blood lymphocyte (PBL) fraction. Methods for isolating PBLs from whole blood are well known in the art. In addition, it is possible to use a blood sample and enrich the small amount of circulating cells from a tissue of interest, e.g., ovaries, breast, etc., using methods known in the art.

Fine needle aspiration (FNA) has demonstrated to be a robust and safe method to acquire tumor material in sufficient quantities to assess pharmacodynamic endpoints in a serial manner. In addition, preliminary evidence is provided suggesting that this methodology can be efficiently used in procuring tissue to reproduce in vitro conditions and develop an ex vivo molecular sensitivity and resistance assay. This approach has classically drawn considerable interest and the outcome and ultimate significance of a number of these studies has been the subject of recent reviews. Most studies analyzed whether cells derived from a sample of viable tumor tissue show a response when exposed to selected therapeutic agents under in vitro conditions. Thus, in one embodiment, the assay is based on fine needle aspiration of any lesion and processing the aspirated material for protein and/or nucleic acid analysis. Depending on the particular pharmaceutical agent used, the assay allows for determination of sensitivity of the lesion to treatment, effectiveness of specific pathway blockade, and monitoring of therapy effects at the molecular level. The assay can be performed with minimal morbidities and discomfort, and can be used for drug sensitivity assessment, dosing regimen, therapy effect measurement, and prognostication.

SnapPath™ Ex Vivo Biomarker Platform: Fine needle aspiration biopsies (FNABs) are a minimally-invasive method for sampling human tumors that is widely used in the United States. Historically FNAB samples have provided adequate material for microscopic examination, however the successful development and use of targeted cancer drugs will also require biomarker information derived from these clinical samples.

While ex vivo biomarkers have been used successfully in various clinical trials using manual live tissue manipulation at the patient's bedside. Ex vivo tests are not clinically feasible unless an automated, rapid processing device, such as SnapPath™ exists. The ability to interrogate live tumor cells with novel ex vivo biomarker tests to determine the most effective cancer treatment for individual patients is the promise of the SnapPath™ biomarker platform.

SnapPath™ benchtop units will utilize automated fluidic technologies to process and manipulate live tumor biopsy samples, within uniquely designed insertible cartridges. In the SnapPath™ system, radiologists will deposit (FNA) biopsy samples into a SnapPath™ cartridge immediately after the needle is removed from the patient. Cartridges will then be rapidly delivered to pathology where the SnapPath™ platform will be located, in a process similar to that required for lymphoma samples processed by flow cytometry.

The SnapPath™ biomarker platform is being developed with a $2.3 million Fast-Track SBIR contract from the National Cancer Institute. In the NCI's contract award, the agency stated that the company's SnapPath™ technology presented an "innovative" FNA biopsy approach and instrument that was "extremely responsive" to the NCI's contract announcement which expressed interest in "biopsy instruments and devices that preserve molecular profiles in tumors," including those that will "create an entirely new diagnostic area" and "enable individualized molecular therapy of solid tumors based on accurate information about signal transduction pathways, molecular drug targets and biomarkers." The NCI also recently stated that technologies focusing on ex vivo diagnostics and ex vivo tissue-analysis are a "priority" for the NCI's SBIR Phase II Bridge Award program.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In addition, the term "subject" may refer to a culture of cells, where the methods of the invention are performed in vitro to assess, for example, efficacy of a therapeutic agent.

As used herein, the terms "molecule" or "biomolecule" refer to any organic molecule in a living organism. Exemplary biomolecules include, but are not limited to, peptides, lipids, nucleic acids, metabolites, and carbohydrates. In one embodiment, the biomolecule is a peptide, such as a protein, or a nucleic acid molecule. The terms "polypeptide," "peptide" and "protein" are used interchangeably herein to refer to two or more amino acid residues joined to each other by peptide bonds or modified peptide bonds, i.e., peptide isosteres. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, for example, a particular gene of interest, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

As used herein, the term "EGFR modulator" refers to a compound or drug that is a biological molecule or a small molecule that directly or indirectly modulates EGFR activity or the EGFR signal transduction pathway. Compounds or drugs as used herein is intended to include both small molecules and biological molecules. Direct or indirect modulation includes activation or inhibition of EGFR activity or the EGFR signal transduction pathway. Inhibition refers to inhibition of the binding of EGFR to an EGFR ligand including, for example, EGF. In addition, inhibition can also refer to inhibition of the kinase activity of EGFR.

EGFR modulators include, for example, EGFR specific ligands, small molecule EGFR inhibitors, and EGFR monoclonal antibodies. In one aspect, the EGFR modulator inhibits EGFR activity and/or inhibits the EGFR signal transduction pathway. In another aspect, the EGFR modulator is an EGFR antibody that inhibits EGFR activity and/or inhibits the EGFR signal transduction pathway.

EGFR modulators include biological molecules or small molecules. Biological molecules include all lipids and polymers of monosaccharides, amino acids, and nucleotides having a molecular weight greater than 450. Thus, biological molecules include, for example, oligosaccharides, polysaccharides, oligopeptides, polypeptides, peptides, proteins, oligonucleotides, and polynucleotides. Oligonucleotides and polynucleotides include, for example, DNA and RNA. Biological molecules further include derivatives or combination of any of the molecules described above. For example, derivatives of biological molecules include lipid and glycosylation derivatives of oligopeptides, polypeptides, peptides, and proteins.

In addition to the biological molecules discussed above, the EGFR modulators useful in the invention may also be small molecules. Any molecule that is not a biological molecule can be considered herein to be a small molecule. Some examples of small molecules include organic compounds, organometallic compounds, salts of organic and organometallic compounds, saccharides, amino acids, and nucleotides. Small molecules further include molecules that would otherwise be considered biological molecules, except their molecular weight is not greater than 450. Thus, small molecules may be lipids, oligosaccharides, oligopeptides, and oligonucleotides and their derivatives, having a molecular weight of 450 or less.

It is noted that small molecules are merely called small molecules because they typically have molecular weights less than 450. Small molecules include compounds that are found in nature as well as synthetic compounds. In one embodiment, the EGFR modulator is a small molecule that inhibits the growth of tumor cells that express EGFR. In another embodiment, the EGFR modulator is a small molecule that inhibits the growth of refractory tumor cells that express EGFR. Numerous small molecules have been described as being useful to inhibit EGFR and are well known in the art.

The invention also includes specialized microarrays, e.g., oligonucleotide microarrays or cDNA microarrays, comprising one or more biomarkers, showing expression profiles that correlate with either sensitivity or resistance to one or more stimulations, for example EGFR modulators. Such microarrays can be employed in in vitro assays for assessing the expression level of the biomarkers in the test cells from tumor biopsies, and determining whether these test cells are likely to be resistant or sensitive to stimulations, for example EGFR modulators. Cells or live tissue samples from a subject can be isolated and exposed to one or more of stimulations, for example the EGFR modulators. Following application of nucleic acids isolated from both untreated and treated cells to one or more of the specialized microarrays, the pattern of gene expression of the tested cells can be determined and compared with that of the biomarker pattern from the control panel of cells used to create the biomarker set on the microarray. Based upon the gene expression pattern results from the cells that underwent testing, it can be determined if the cells show a resistant or a sensitive profile of gene expression.

The invention also includes kits for determining or predicting whether a patient would be susceptible or resistant to a treatment that includes one or more stimulations, for example EGFR modulators. The patient may have a cancer or tumor such as, for example, a breast cancer or tumor. Such kits would be useful in a clinical setting for use in testing a patient's cancer samples, for example, to determine or predict if the patient's tumor or cancer will be resistant or sensitive to a given treatment or therapy. The kit includes a suitable container that includes one or more microarrays, e.g., oligonucleotide microarrays or cDNA microarrays, that include those biomarkers that correlate with resistance and sensitivity to stimulations, for example EGFR modulators, particularly EGFR inhibitors; one or more stimulations, for example EGFR modulators for use in testing cancer samples or cells from a patient; and instructions for use. In addition, kits contemplated by the invention can further include, for example, reagents or materials for monitoring the expression of biomarkers of the invention at the levels of mRNAs or proteins, using other techniques and systems practiced in the art such as, for example, RT-PCR assays, which employ primers designed on the basis of one or more of the biomarkers, immunoassays, such as enzyme linked immunosorbent assays (ELISAs), immunoblotting, e.g., Western blots, or in situ hybridization, and the like.

In one embodiment, the protein is a post-translationally modified protein, where the protein is modified by one or more of phosphorylation, acetylation, amidation, methylation, nitrosylation, fatty acid addition, lipid addition, glycosylation, and ubiquitination.

In another embodiment, the methods further include exposing the sample to one or more therapeutic agents or combination thereof. For solid tumor or other cancer applications, the therapeutic agents can include a targeted pharmaceutical agent such as, for example, antitumor monoclonal antibodies, e.g. trastuzumab (Herceptin®), cetuximab (Erbitux®), bevacizumab (Avastin®) and rituximab (Rituxan® and/or Mabthera®), and small molecule inhibitors, e.g., gefitinib (Iressa®), or erlotinib (Tarceva®) or cytotoxic chemotherapy agents.

Exemplary chemotherapeutic agents also include, but are not limited to, antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-α, etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis. Thus, in one embodiment, the therapeutic regimen is a administration of cisplatin in combination with paclitaxel.

In another aspect, the invention provides a method of predicting the effect of an agent or combination of agents. The method includes determining the difference between a basal level or state of a molecule in a sample and the level or state of the molecule after stimulation of a portion of the sample with a modulator ex vivo, wherein the difference in the basal level or state of the molecule expressed as a value is indicative of a positive or negative effect of the agent. In one embodiment, the agent interacts directly with the molecule in the sample. In another embodiment, the effect is the activation or inhibition of a cellular pathway selected from the group consisting of a metabolic pathway, a replication pathway, a cellular signaling pathway, an oncogenic signaling pathway, an apoptotic pathway, and a pro-angiogenic pathway.

In another aspect, the invention provides a method of screening test agents for an effect on a molecule. Thus, the effects of the presence or absence of a test agent can also be determined by detecting an ex vivo biomarker, for example, a post-translationally modified protein, ions, or enzymes. The method includes contacting a sample containing the molecule or molecules with the test agent ex vivo, then determining a difference between a basal level or state of the molecule in the sample and the level or state of the molecule after stimulation of a portion of the sample with a modulator ex vivo; wherein a difference in the basal level or state of the molecule before and after contacting with the test agent is indicative of an effect on the molecule.

Suitable test agents include, but are not limited to, one or more of the following: small molecule chemical, a chemotherapeutic agent, a hormone, a protein, a peptide, a peptidomimetic, a protein, an antibody, a nucleic acid, an RNAi molecule, and an antisense molecule. In one embodiment, the administration of a test agent can be followed by measuring a quantitative or qualitative effect on a target ex vivo biomarker or biomolecule of the dispersed or distributed cell.

In another embodiment, it can be determined if the test agent affects the expression of one or more markers, wherein the presence, absence, or relative degree of such expression is indicative of the susceptibility of the cells to a selected pharmaceutical agent. These markers can include a wide array of ex vivo biomarkers such as mRNA, a microRNA, cDNA, a protein, a phosphoprotein, a posttranslational modification of a protein, or a modification of histone or DNA packaging. For example, the marker can be mRNA or cDNA for an early response gene (e.g., FOS or JUN) associated with susceptibility to a pharmaceutical agent. The presence, absence, or relative degree of expression of combinations of markers in the presence of a test reagent can be indicative of the susceptibility of the cells to a selected test reagent, such as a pharmaceutical agent.

For certain analytical methods, the test agent can be a detectable agent. The detectable agent can be used individually or as conjugated or otherwise connected to another compound (e.g., a detectable agent conjugated to an antibody). Suitable detectable agents include, but are not limited to, an enzyme, fluorescent material, luminescent material, bioluminescent material, radioactive material, positron emitting metal using a positron emission tomography, or a nonradioactive paramagnetic metal ion.

Once disease is established and a treatment protocol is initiated, the methods of the invention may be repeated on a regular basis to evaluate whether the level or intensity of symptoms related to the disease in the subject begins to approximate that which is observed in a normal subject. The results obtained from successive assays may be used to show the efficacy of treatment over a period ranging from several days to months. Accordingly, the invention is also directed to methods for monitoring the course of a subject's therapy. The method includes determining the difference between a basal level or state of a molecule in a sample and the level or state of the molecule after stimulation of a portion of the sample with a modulator ex vivo, optionally prior to, simultaneously with or following a course of therapy; wherein the difference in the basal level or state of the molecule expressed as a value is indicative of a positive or negative treatment. Thus, a positive treatment is indicative of the subject being a responder to the course of therapy. Likewise, a negative treatment is indicative of the subject having resistance to the course of therapy.

In one embodiment, the method may further include comparing the level of the signs and symptoms related to the disease prior to and during therapy, where a lessening of the signs and symptoms of disease indicates the efficacy of the therapy. Therefore, one skilled in the art will be able to recognize and adjust the therapeutic approach as needed.

The methods described herein may be performed with or without a cartridge as described in U.S. Publication No. 2009/0162853, incorporated herein by reference. An advantage of the methods and devices herein is that the test agent can be added at the point of care and/or can come preloaded in specified wells of the cartridge. This allows the testing of ex vivo biomarkers, optionally near the point of care, using live cells. These methods and devices can be used with specific test agents to manipulate samples ex vivo to facilitate the development of novel predictive biomarkers, monitor and determine cellular sensitivity to specific pharmaceutical agents, and other uses that one of skill in the art will appreciate.

For example, a sample of a solid tumor from a patient can be disaggregated, distributed, and then tested against a panel of currently available cancer therapeutics at the point of care. The samples can then be stabilized and/or fixed if necessary and analyzed. Depending on the results for each test agent, the physician can quickly determine which therapeutics will be most effective on the individual patient's tumor at or near the point of care. This personalized medicine provides numerous benefits, in particular, the use of targeted cancer therapeutics and regimens in a rapid, cost effective manner.

Embodiments of the invention are directed to analyzing the distributed cells (e.g., cancer cells) by administering at least one agent to produce a measurable quantitative or qualitative effect on a target ex vivo biomarker or biomolecule. The quantitative or qualitative effect can be the activation or inhibition of a cellular pathway. Exemplary cellular pathways include, but are not limited to, a metabolic pathway, a replication pathway, a cellular signaling pathway, an oncogenic signaling pathway, an apoptotic pathway, and a pro-angiogenic pathway. For example, the quantitative or qualitative effect can be a measurement of an agonistic or antagonistic effect on a G-protein coupled receptor or a receptor tyrosine kinase, such as, epidermal growth factor receptor (EGFR) and the downstream pathways.

In various embodiments, the cells and/or molecules are analyzed using one or more methods selected from an array, enzyme-linked immunosorbent assay (ELISA), multiplex, bioplex, luminex, mass spectrometry, flow cytometry, Northern blot, Southern blot, Western blot, and radioimmunoassay (RIA). In other embodiments, cells and/or molecules are analyzed using any apparatus known in the art for analyzing nucleic acids. In other embodiments, the difference between a basal level or state of a molecule in a sample from a subject and the level or state of the molecule after stimulation of a portion of the sample with a modulator ex vivo is determined using a computer.

In another aspect, the invention provides a method for stratification of patients based on responsiveness to a therapeutic agent or therapeutic regimen. The method includes determining the difference between a basal level or state of a molecule in a sample from a subject and the level or state of the molecule after stimulation of a portion of the sample with a modulator ex vivo; wherein the difference in the basal level or state of the molecule expressed as a value is indicative of a positive or negative response to a therapeutic agent or therapeutic regimen. Thus, a positive response is indicative of the subject being a responder to the course of therapy. Likewise, a negative response is indicative of the subject having resistance to the course of therapy.

As described herein, the cells processed using the present invention can be prepared and stabilized in a number of ways to permit a wide array of cellular analyses to be performed on them. For example, the cells can be prepared for nucleic acid analysis, protein analysis, and/or analyzed using live cellular probes.

For nucleic acid analysis, a stabilizing reagent such as RNAlater®, RNA Protect Cell Reagent® (both available from Qiagen), or ethanol can be added to the cells. The stabilized cells can then be optionally lysed or have the nucleic acid of interest otherwise extracted. The extracted and purified nucleic acid can then be analyzed, for example, using PCR techniques.

In some embodiments, the methods described herein yield nucleic acid molecules for further analysis. For these samples, following dispersion and optional enrichment, the nucleic acids can be stabilized or extracted (optionally) to yield high quality and quantity nucleic acid molecules. This can be done, for example, by lysing the desired cells following exposure to a test agent and then obtaining cDNA using reverse transcriptase and DNA primers. The DNA primers can include nonspecific primer complementary to poly A, e.g. oligo(dT)12-18 or a specific primer complementary to a mRNA transcript of interest. As one of skill in the art will appreciate, the cells can be lysed using a variety of methods, such as, chemical or mechanical means.

Optionally, the cells can be stabilized with reagents to detect and/or preserve biomarker information, e.g., using reverse transcriptase and DNA primer to obtain cDNA transcripts, preparing RNA, DNA and protein for down stream molecular analysis.

For protein or nucleic acid analysis, either whole cells or lysed cells can be used. Intact whole cells can be fixed and stabilized with a polymer, such that the sample adheres to the isolated chamber, for example, a glass slide. These samples can then be subjected to analysis, for example, immunohistochemical (IHC) analysis. Lysed or otherwise ruptured cells can be used in assays such as Western Blots and may not require stabilization or fixation.

Slide preparation for morphological review by a pathologist and protein analysis by IHC can be an output of the methods described herein. Accordingly, the cells can also be prepared, optionally using polymers, on glass slides for analysis of morphology and/or immunohistochemistry.

Live cellular probe analysis can involve adding a molecular probe (such as MitoTracker®) at any point in the method of processing the cells where the cells are alive. This addition of the live cell probe should be made prior to fixing or otherwise allowing the cells to die. For example, such a probe can be added before or after cellular stabilization but prior to cellular fixation.

In some embodiments, the cells can be stabilized and fixed by any suitable means that will permit subsequent molecular analysis and detection of markers. Generally, crosslinking fixatives such as formalin are not preferred but may be present in small amounts that will not interfere with subsequent analysis. Where the biomarker is expression of a particular gene or genes, in one embodiment the cells are lysed and exposed to reverse transcriptase and suitable primers, so as to generate cDNA transcripts of mRNA transcripts in the cells. This facilitates subsequent analysis, as cDNA is less subject to degradation than mRNA.

In some embodiments, $1 \times 10^4$ or more cells are processed to stabilize any or all of the following: RNA, DNA, protein, and/or phosphoproteins.

In some embodiments, the cells can be fixed after processing. Any suitable means of fixation can be used, for example, air drying techniques, adding a compound such as alcohol, e.g., a fixative comprising a lower alkanol, e.g., methanol or ethanol, adding formalin, adding an RNase inhibitor, adding agarose, adding polyethylene glycol, adding poly 1-lysine, or adding one or more chelator or antioxidant. In some embodiments, the fixative includes agarose, polyethylene glycol, octylphenoxy-polyethylene glycol, poly-1-lysine, reagent alcohol and water.

In another aspect, the methods of the present invention include a method for preparing solid tissue cells from a subject, e.g., solid tumor cells from an animal or human subject having a solid tumor, e.g., for determination of sensitivity of the cells to a selected targeted pharmaceutical agent. An example method can include the steps of (a) obtaining solid tissue comprising desired cells from the subject; (b) dispersing (e.g., using shear forces) the tissue into single live cells and/or aggregates of not more than 100 live cells, e.g., 10 to 100 cells; (c) enriching the sample, e.g. removing contaminating materials from the live cells; (d) distributing the live cells into test aliquots in isolated chambers; (e) exposing the live cells to one or more test reagents; and (f) treating the cells with a fixative and/or stabilizing agent (e.g., an agent stabilizing RNA, DNA, proteins and/or phosphoproteins) to fix the tumor cells and/or marker for further analysis; wherein the fixation of the tumor cells and/or the marker is completed within four hours of removal of the tissue from the subject in an automated or manual fashion.

Another embodiment of the invention provides a method of testing cells wherein solid tumor cells are removed from a mammal (e.g., a human patient), and while most of the cells, e.g., at least 65% of the cells, e.g., at least 75% of the cells are viable and have not replicated outside the body, exposing all or a portion of the cells ex vivo to one or more test reagents, and stabilizing the cells, optionally with a fixative (e.g., a polymer) that can preserve biomarker information including cellular DNA, RNA, proteins, and/or phosphoproteins. These biomarkers can be tested using molecular analyses known to one of skill in the art or using the novel ex vivo biomarker tests disclosed herein.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Functional Signal Profiles of Phosphoprotein Array

FIG. 1 is a bar chart that summarizes data derived from a phosphoprotein array that contains 29 different phosphoproteins. The data are derived from 3 breast cancer cell lines that have been treated with EGF. The bars represent up-regulation of the phosphoprotein relative to the basal state without EGF stimulation. Note that these cell lines display very different sets of up-regulated phosphoproteins upon EGF stimulation giving information about the signal transduction networks of these cells.

Using raw data similar to that provided herein, an algorithm will be used to create a "profile" for each tumor. For example, the level of each individual phosphoprotein will be assigned a "score" between 0, low, medium and high, based on previously determined cut values. Then the scores from each analyzed protein within a tumor will be assembled into a group termed the functional signaling profile. Each profile will provide information about the functional status of the tumor cell which can then be used to predict the targeted drug sensitivity/resistance of the tumor. An example of such functional signaling profiles for a set of five breast cancer cell lines is shown in FIGS. 2A and 2B.

Example 2

Functional Stratification of Breast Carcinoma Cells Enables Predictive Therapeutic Strategies Most targeted therapies still lack effective predictive biomarkers. A major limitation of the existing classes of biomarkers is the lack of functional information about the signal transduction networks targeted by molecularly targeted drugs. The present invention provides a functional assay based on ex vivo biomarkers produced by live tumor cells. The profile is elicited by short-term epidermal growth factor (EGF) stimulation in the presence or absence of a MEK inhibitor. The resultant changes in signal transduction phosphoprotein levels are used to create functional signaling profiles that stratify tumor cell lines into functional groups. This functional signaling profile is feasible by an automated platform that is amenable to tumor biopsy processing.

Breast Cancer Cell lines (BT-474, MDA-MD-231, SKBR3, HCC-1937, BT-20, T47D, MCF-7, BT-549) are propagated and removed from the plate by gentle scraping to simulate a FNA biopsy sample. Following removal, the cells were placed on the SnapPath™ live-tumor-cell processing platform (BioMarker Strategies, LLC) to evoke ex vivo biomarkers. SnapPath™ disperses the sample, enriches for tumor cells, aliquots into test wells, and applies ex vivo stimulation by EGF (200 ng/ml) in the presence or absence of the MEK inhibitor, U0126 (1 µM). Cell lysates are then analyzed using the BioPlex platform for the following phosphoproteins: p-Erk 1/2, p-AKT, p-EGFR, p-Stat3 (Bio-Rad). Functional profiles are generated for each cell line based on the levels of phosphoproteins.

Functional signaling profiles of breast cancer cell lines stimulated with EGF in the presence of U0126 reveal distinct functional groups that enabled the stratification. Two functional groups are identified based on pAKT phosphorylation levels: one group displays variable, but low levels of p-AKT inhibition, whereas another group shows unanticipated up-regulation of p-AKT. This second group may be resistant to MEK inhibition but sensitive to the combination of MEK/AKT inhibition. Two other functional groups are identified based on pEGFR phosphorylation levels: one group displays variable, but low p-EGFR inhibition, whereas the other group shows unanticipated up-regulation of p-EGFR. This second group may be resistant to MEK inhibition, but sensitive to combined MEK/EGFR inhibition.

Functional signaling profiles of human cancers reveal unique details of signal transduction networks that permit stratification of tumors unavailable through traditional biomarkers. These profiles may correlate with targeted drug sensitivity or resistance and may yield successful companion diagnostics, including combination therapies of targeted agents. Such functional profiles can be reproducibly elicited from small numbers of tumor cells on an automated platform, suggesting that this approach to predictive tests is possible for human tumor biopsy samples.

Example 3

Stratification of Breast Cancers Based on Functional Phosphoprotein Signaling Profiles Elicited from Live Tumor Cells Abnormal signal transduction networks are frequent targets of existing and emerging molecularly targeted agents (MTAs). Unfortunately, most predictive biomarkers to guide therapeutic selection are based on indirect assessment of signal transduction through DNA mutations or transcriptional profiles rather than dynamic assessment of signal transduction proteins themselves. Classification of breast cancer based on functional signaling profiles derived from a set of signaling phosphoproteins induced upon growth factor stimulation of live breast cancer cells is likely to provide a more accurate system for MTA selection than indirect methods utilizing fixed or frozen tissue.

Figure 3:
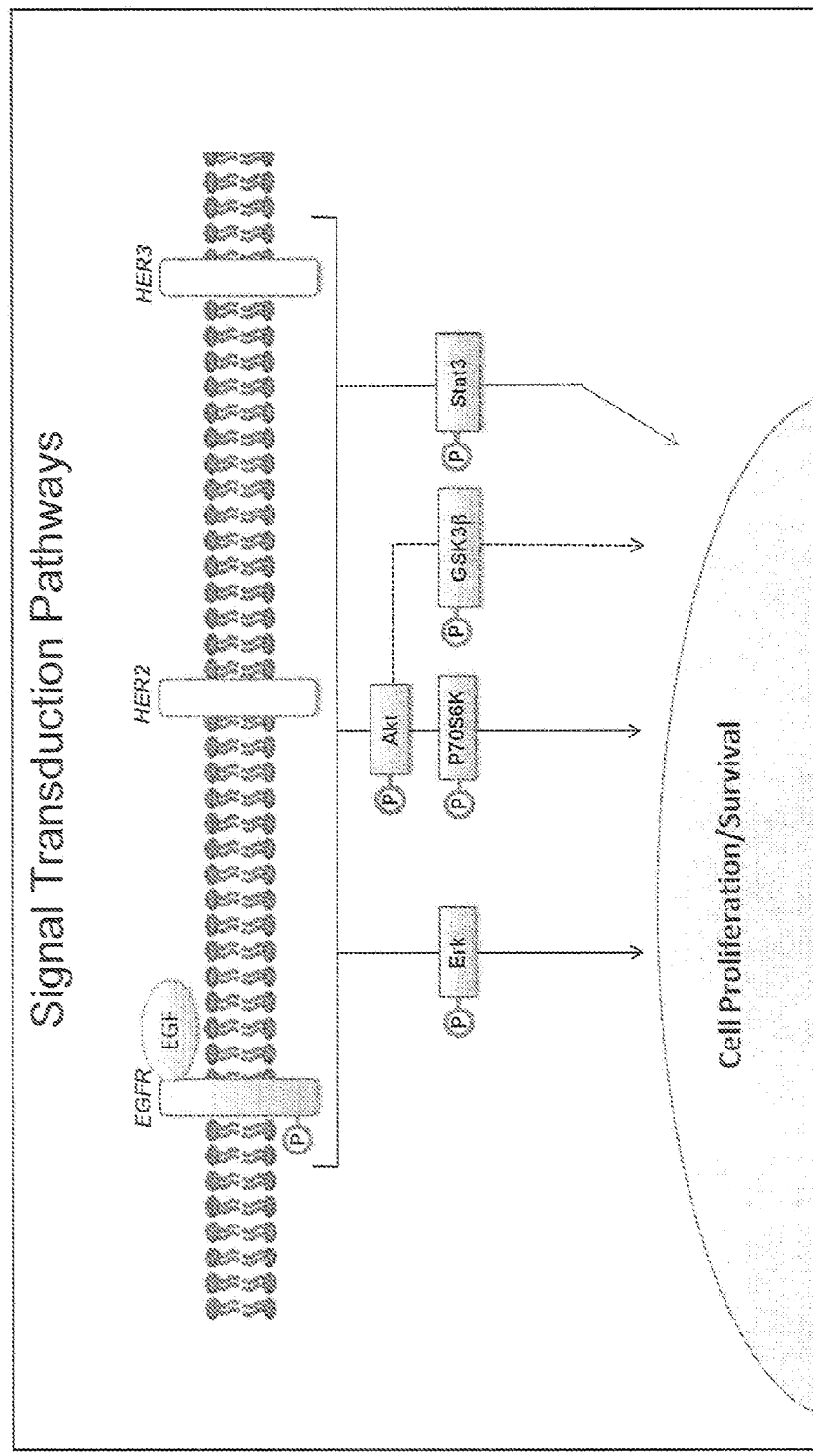
FIG. 3 shows an exemplary illustration of signal transduction pathway used by the present invention.
Figure 4:
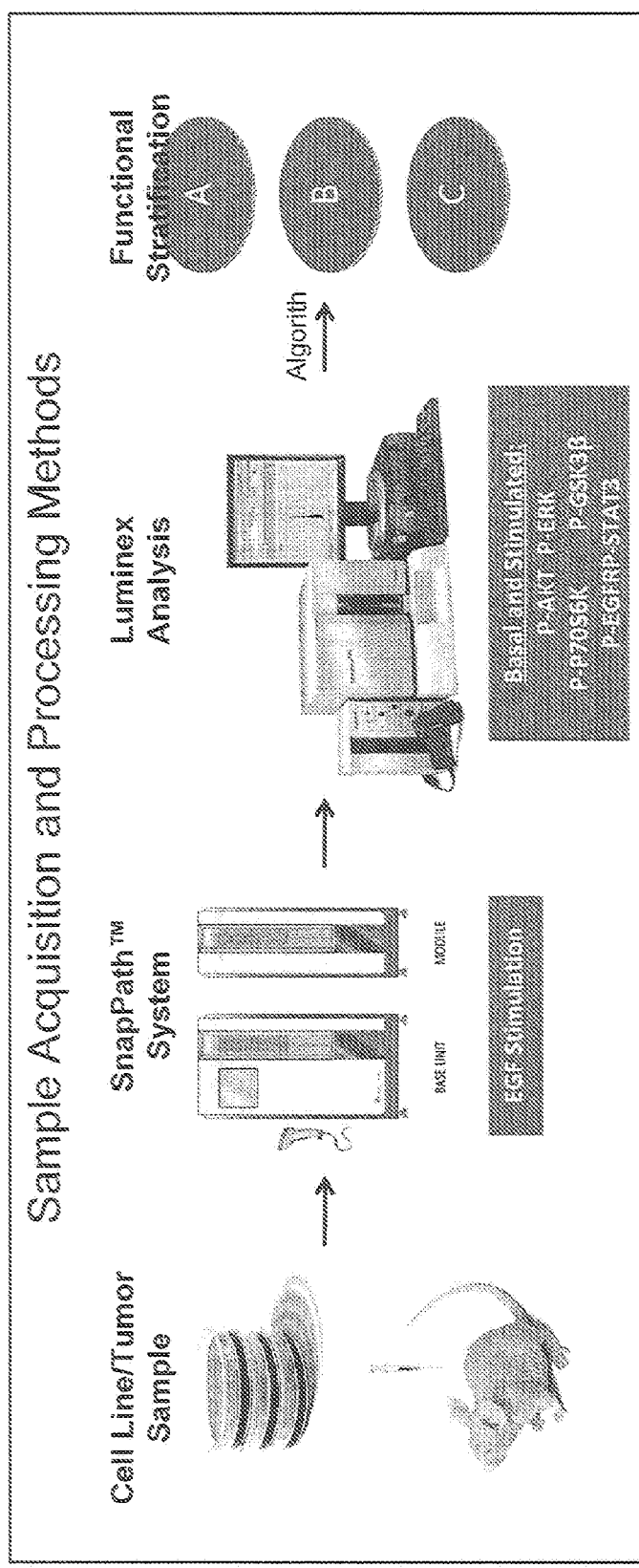
FIG. 4 shows an exemplary process flowchart of the present invention. Live tumor samples are typically obtained from a subject and then at least one stimulation is applied to trigger signal transduction events in the live tumor samples. Basel levels and stimulated levels of various mRNA or proteins can be evaluated and then functional stratification can be determined.
Figure 5:
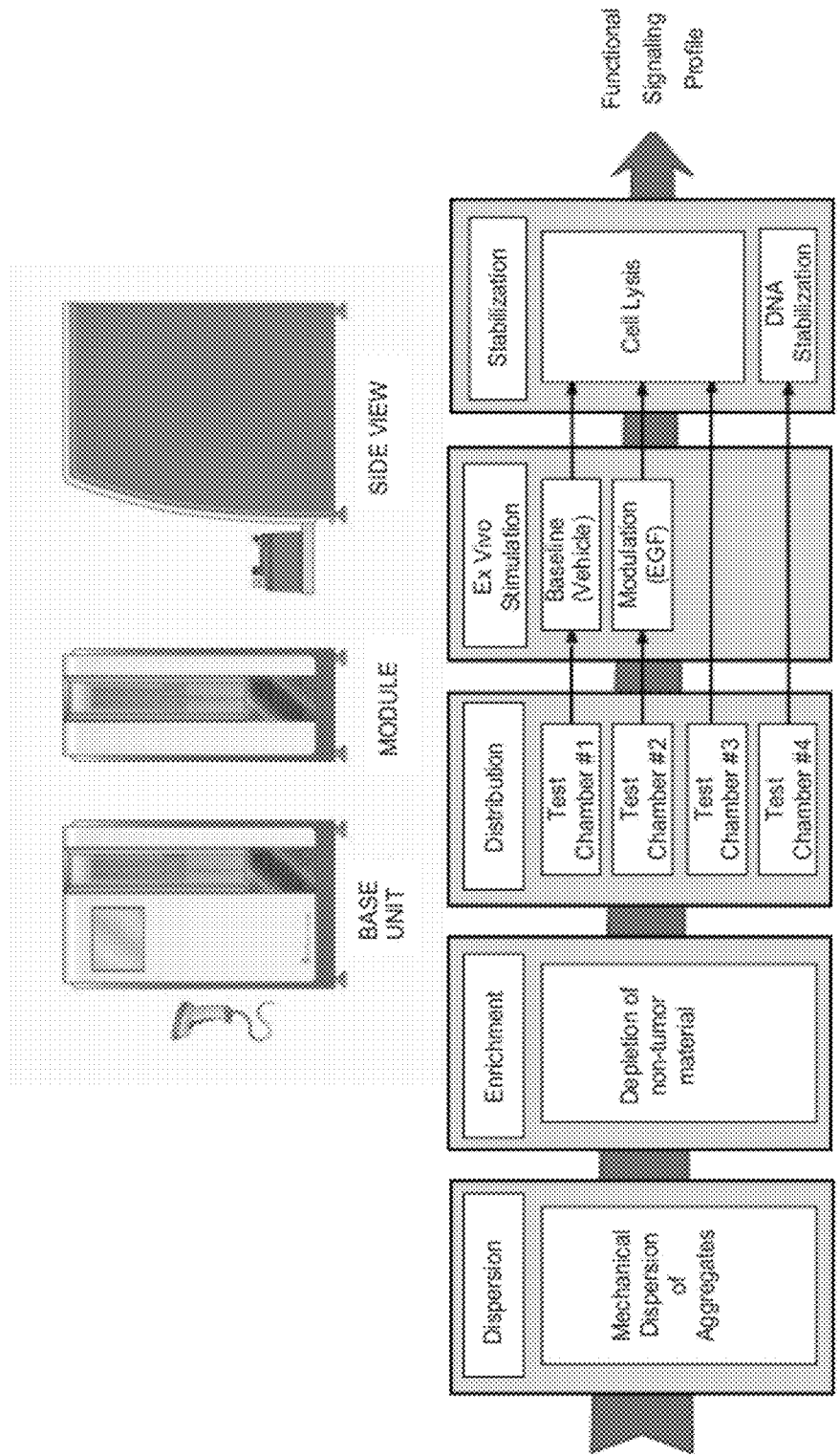
FIG. 5 shows an exemplary illustration for various steps/equipments to apply stimulations to live tumor samples of a subject.

This example provides demonstration for stratification of multiple breast cancer model systems based on functional signaling profiles elicited from live tumor cells in response to ex vivo stimuli. Breast cancer cell lines (MCF-7, HCC-1937, MDA-MB-231, BT474, and SKBR3) are exposed to either vehicle (control) or stimulated with 200 ng/ml epidermal growth factor (EGF) for 5 minutes then lysed and proteins extracted. The signal transduction pathway involving EGF is shown in FIG. 3. Mean Fluorescence Intensity (MFI) levels of six phosphoproteins (pEGFR, pErk, pAKT, pP70S6K, pGSK3β, and pSTAT3) are determined in sextuplet using a multiplexed bead-immunoassay (BioPlex, Bio-Rad) and a modulation score (MS), defined as the log 2 (MFI stimulated/MFI control), calculated for each. The sample acquisition and processing methods are shown in FIGS. 4 and 5. Scores are ranked by percentile relative to the median (0.66) and inter-quartile range (IQR) (1.54). Moderate responders are classified as those with MS between the 75th percentile (2.20) and the 75th percentile plus the IQR (3.74). High responders are those MS>3.74. Low responders are those MS falling between the IQR and 75th percentile (1.54-2.20) whereas non responders are classified as MS<1.54.

Figure 6:
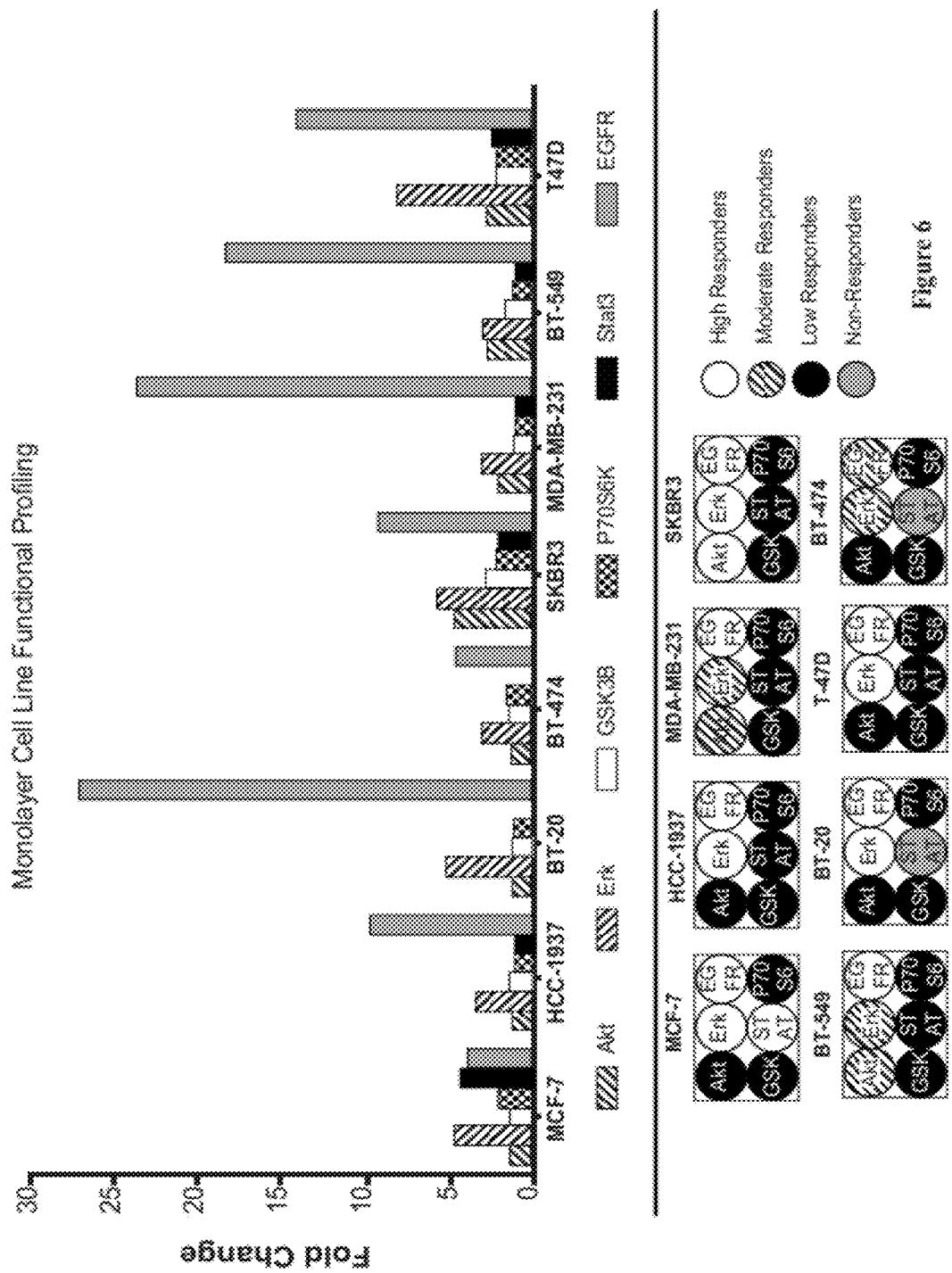
FIG. 6 shows functional stratification of several breast cancer cell lines. The upper left chambers are for AKT. The upper middle chambers are for Erk. The upper right chambers are for EGFR. The lower left chambers are for GSK3Beta. The lower middle chamber are for STAT3. The lower right chambers are for P70S6K.

Functional stratification of breast cancer cell lines tested are shown in FIG. 6, and the cell line hierarchal clustering based on functional stratification is shown in FIG. 7. EGF stimulation results in high levels of EGFR-phosphorylation in all cells except BT474, which responds moderately (2.57). MS for pErk are high in MCF-7 cells (3.92), moderate in HCC-1937 (2.89) and none for the other lines tested. Moderate STAT-3 phosphorylation is observed in only MCF-7 cells (2.34) whereas low pAKT MS are observed in only SKBR3 (1.78). All other markers across the five cell lines tested are non responders (<1.54), with pGSK3β and pP70S6K yielding MS<1.0 for all five cell lines. Interestingly, the relative MS rank order of all six proteins differed across each cell line suggesting further opportunity for stratification.

TABLE 1

SnapPath ™ Processed Cell Line Clustering

| | BT-20 | BT-474 | BT-549 | HCC-1937 | MCF-7 | MDA-MB-231 | SKBR3 | T-47D |
|---|---|---|---|---|---|---|---|---|
| BT-20 | — | 0.33 | 0.93 | 0.90 | 0.18 | 0.96 | 0.15 | 0.62 |
| BT-474 | | — | 0.05 | 0.69 | 0.99 | 0.06 | 0.67 | 0.91 |
| BT-549 | | | — | 0.78 | −0.31 | 0.98 | 0.31 | 0.49 |
| HCC-1937 | | | | — | 0.22 | 0.78 | 0.55 | 0.90 |
| MCF-7 | | | | | — | 0.24 | 0.19 | 0.50 |
| MDA-MB-231 | | | | | | — | 0.17 | 0.46 |
| SKBR3 | | | | | | | — | 0.77 |
| T-47D | | | | | | | | — |

Figure 8:
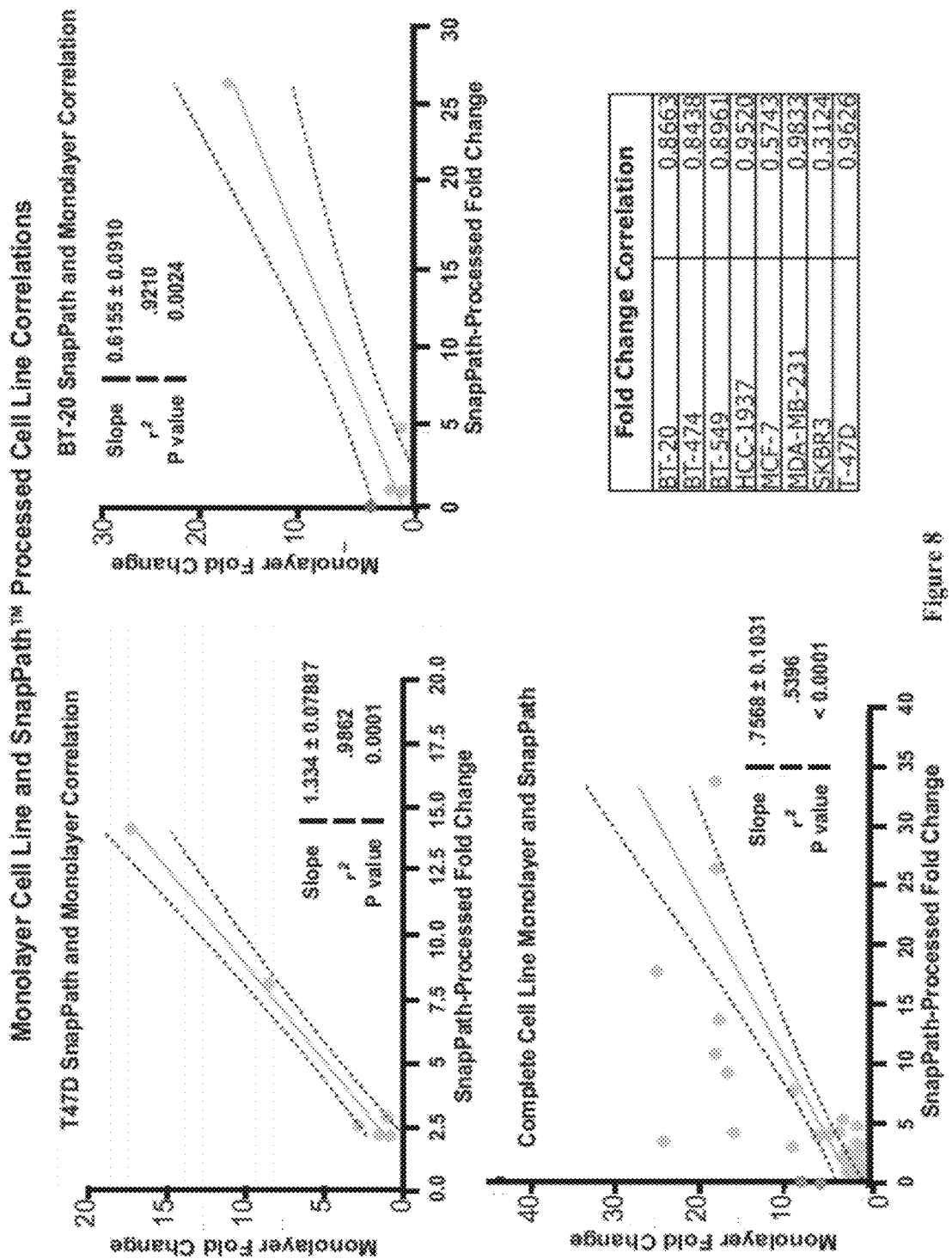
FIG. 8 shows exemplary correlations between monolayer cell line and process cell line (i.e., after simulation such as SnapPath™.
Figure 9:
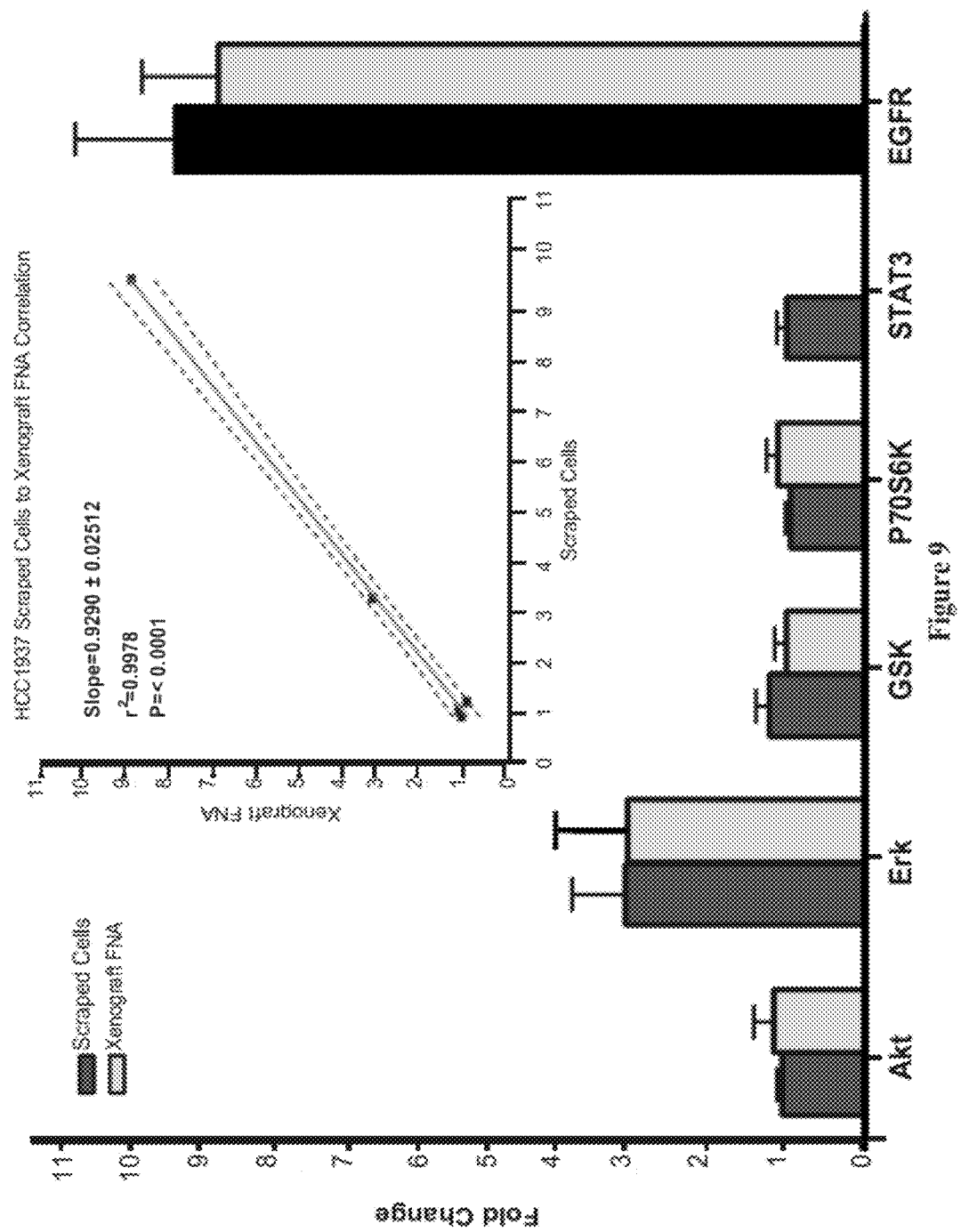
FIG. 9 shows correlations between processed cell line and xenograft for HCC-1937.
Figure 10:
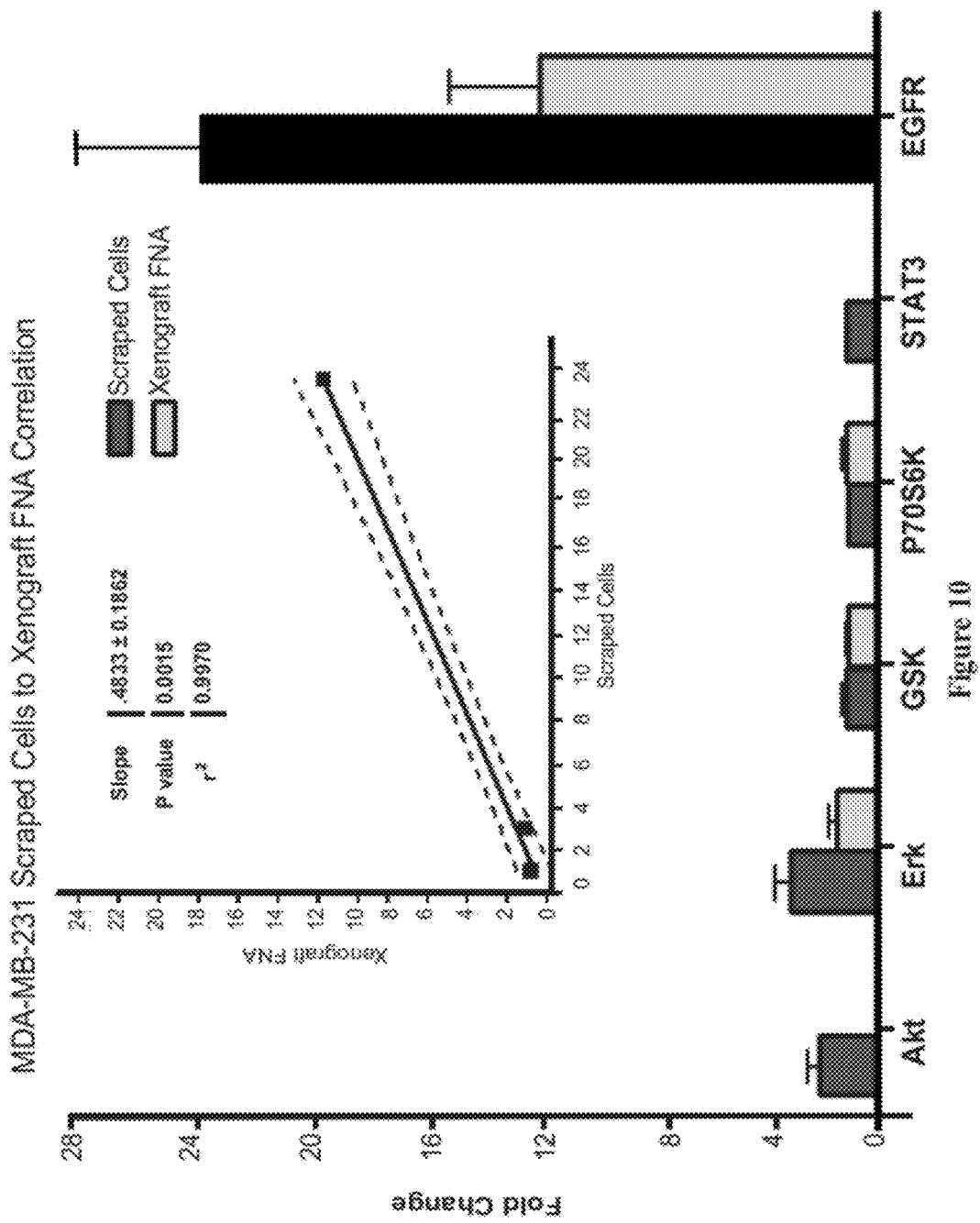
FIG. 10 shows correlations between processed cell line and xenograft for MDA-MB-231.

Correlations between monolayer cell lines and SnapPath™ processed cell lines are shown in FIG. 8, and the processed cell line clustering is shown in Table 1. This example provides that SnapPath™ Enables Functional Stratification in Cell Lines and Xenografts. Correlations between SnapPath™ Processed Cell Line and Xenograft are shown in FIG. 9 (HCC-1937) and FIG. 10 (MDA-MB-231).

Figure 11:
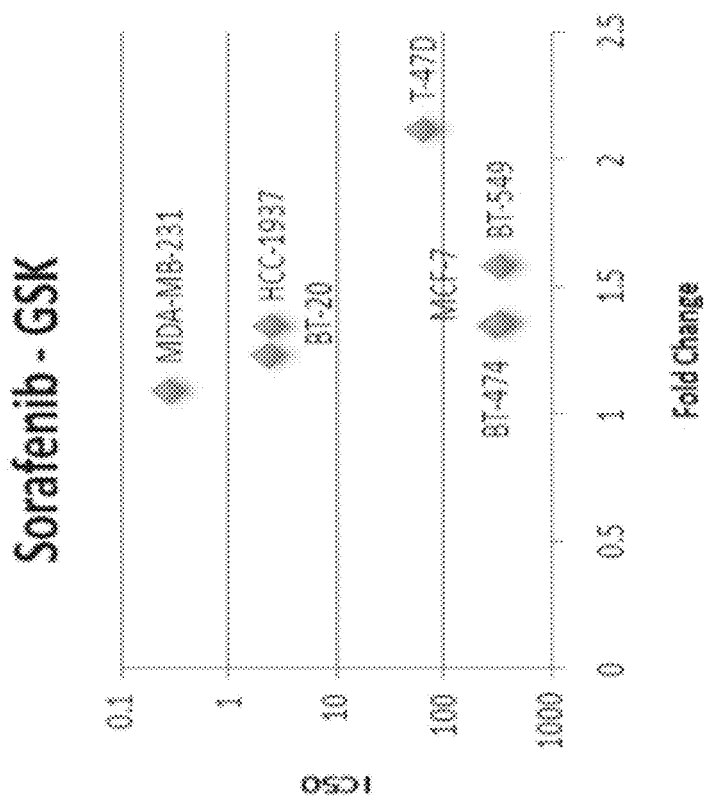
FIG. 11 shows exemplary functional stratification and potential drug correlation, where drug sensitivity and induced fold change after stimulations are illustrated.

FIG. 11 shows relationship between functional stratification and potential drug correlation, where drug sensitivity and induced fold change after stimulations are illustrated.

Figure 12:
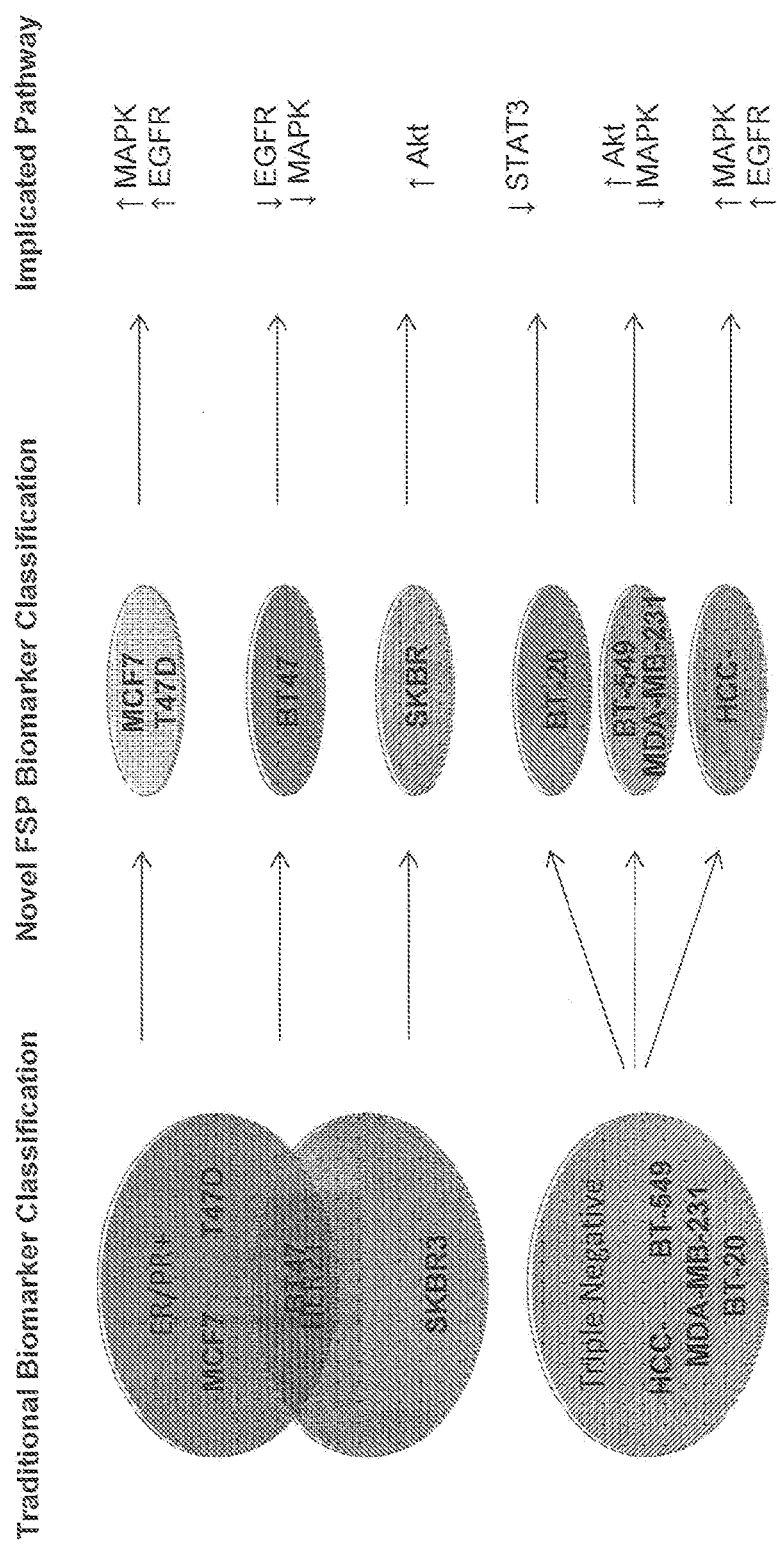
FIG. 12 shows relationship between functional stratification and potential therapeutic options.

FIG. 12 shows relationship between functional stratification and potential therapeutic options. Different breast cancer cell lines display unique functional phosphoprotein signaling profiles, thereby providing a mechanism for stratifying tumors based on individual signal transduction pathway activation.

Figure 13:
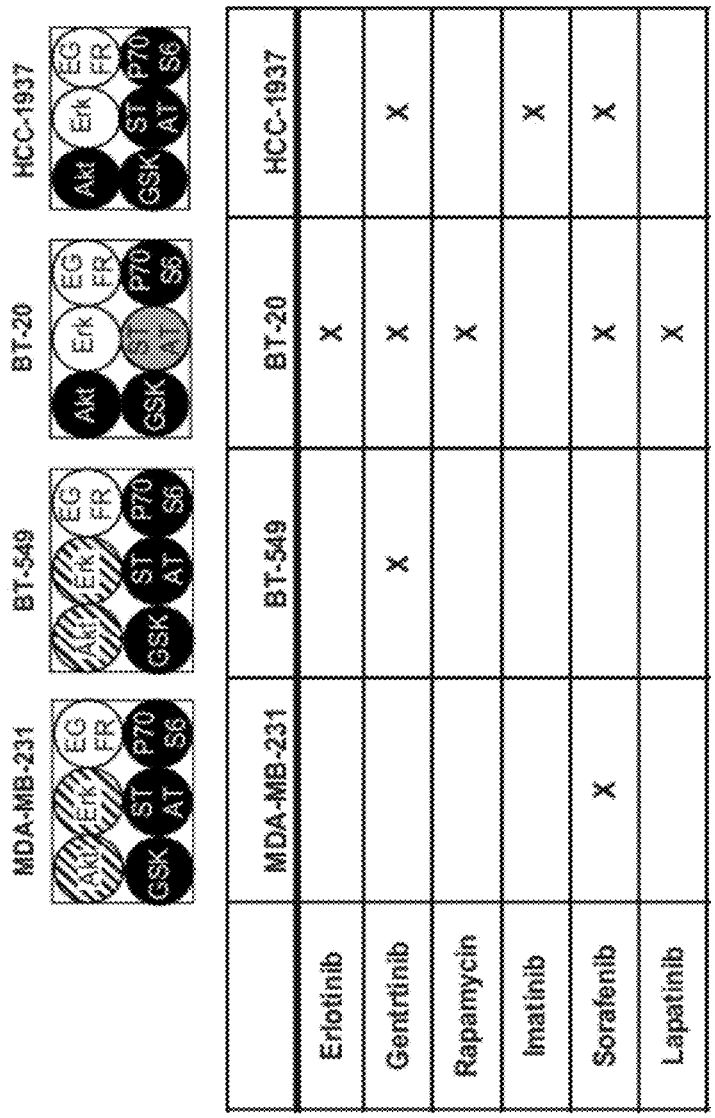
FIG. 13 shows an exemplary illustration where potential drug sensitivity associated with functional signaling profiles of TNBC. The upper row includes pAKT, pErk, and pEGFR. The lower row includes pGSK, pSTAT3, and p70S6k.
Figure 14:
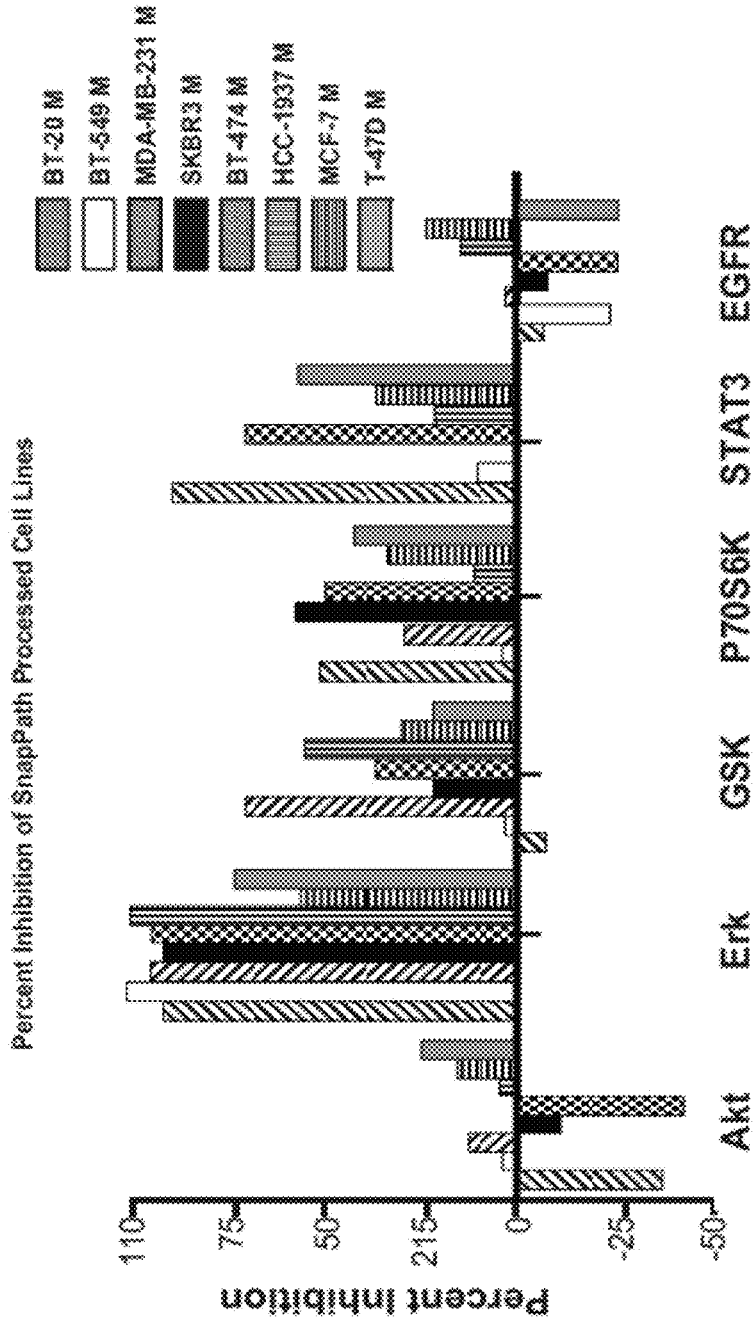
FIG. 14 shows an exemplary illustration where ex vivo stratification and cellular functional circuitry analysis is possible through drug inhibition, and for example, on the SnapPath™ system. This analysis includes pAKT, pErk, pGSK, p70S6k, pSTAT3, and pEGFR.

FIG. 13 shows an illustration where potential drug sensitivity associated with functional signaling profiles of TNBC. The upper row includes pAKT, pErk, and pEGFR. The lower row includes pGSK, pSTAT3, and p70S6k. FIG. 14 shows an illustration where ex vivo stratification and cellular functional circuitry analysis is possible through drug inhibition on the SnapPath™ system. This analysis also includes pAKT, pErk, pGSK, p70S6k, pSTAT3, and pEGFR.

The SnapPath™ system is an automated platform capable of evoking function signaling profiles from cell lines and xenograft tumors. Functional signaling profiles elicited from the SnapPath™ system can be correlated to drug sensitivity and resistance data providing the foundation for a predictive diagnostic platform.

The present invention further provides a method for evaluating a physiological function or toxicity of an agent, compound, a medicament, a poison or the like by using various cells obtained by the methods described herein.

Example 4

Melanoma Functional Signaling Profiles

It has been recognized for several years that melanoma develops through complex and heterogeneous interactions of several molecular pathways that control cellular proliferation, survival and apoptosis.

In particular the RAS-RAF-MEK-ERK pathway seems to play an important role. Approximately 20% of melanomas contain a mutation in NRAS and another 66% contain a mutation in BRAF. In addition to their roles in melanoma pathogenesis, these molecular defects have proven to be useful drug targets. For example, the RAF inhibitor, PLX-4032, has displayed a remarkable response rate in phase I and II clinical trials. Unfortunately, both primary and acquired resistance invariably emerges in patients treated with such RAF inhibitors.

Surprisingly, this resistance has not been attributed to the known mechanism of secondary mutations in the drug binding domain of the target protein. Instead, patients appear to either re-activate the MAPK pathway or utilize an alternate bypass signaling mechanism. Since simple DNA analysis for mutations cannot resolve these resistance mechanisms, a functional assay is an ideal approach to identify resistance and predict appropriate targeted therapy (Soon, Soon et al. The Ochsner Journal 2010; 10(2):93-98; McMahon, M: Parsing out the complexity of RAF inhibitor resistance. Pigment Cell & Melanoma Research. Article first published online: 12 Jan. 2011).

Table 2 summarizes the genotype and phenotype of melanoma cell lines used to elicit function signaling profiles, which represent the spectrum of actual human melanoma samples.

As shown in FIGS. 15-17 and 19-36, functional signaling profiles can distinguish and stratify melanoma samples based on differences in their signal transduction circuitry. Such profiles can be generated by comparing basal levels of various proteins (including pErk, pAKT, pP70S6k, pGSK3β, pEGFR and STAT3) to levels upon exposure of cells to various agents (including EGF, TPA, other growth factors). In addition, perturbing signal transduction networks by exposing the melanoma cells to various agents (such as MEK inhibitors, BRAF inhibitors, etc.) can reveal additional functional information, including the elucidation of drug resistance mechanisms and oncogene bypass mechanisms. Taken together, such functional signaling profiles can form the foundation for prognostic, predictive, pharmacodynamic, or monitoring tests.

TABLE 2

Melanoma cells genotypes and phenotypes for drug resistance

| Melanoma cells | Genotype | PLX-4032 Phenotype |
| --- | --- | --- |
| SK-MEL-31 | BRAF-wt, RAS-wt | Resistant |
| SK-MEL-28 | BRAF-mut (V600E) | Sensitive |
| SK-MEL-2 | NRAS-mut | Unknown |
| RPMI-7951 | BRAF-mut (V600E) COT Amplification | Resistant |

Figure 15:
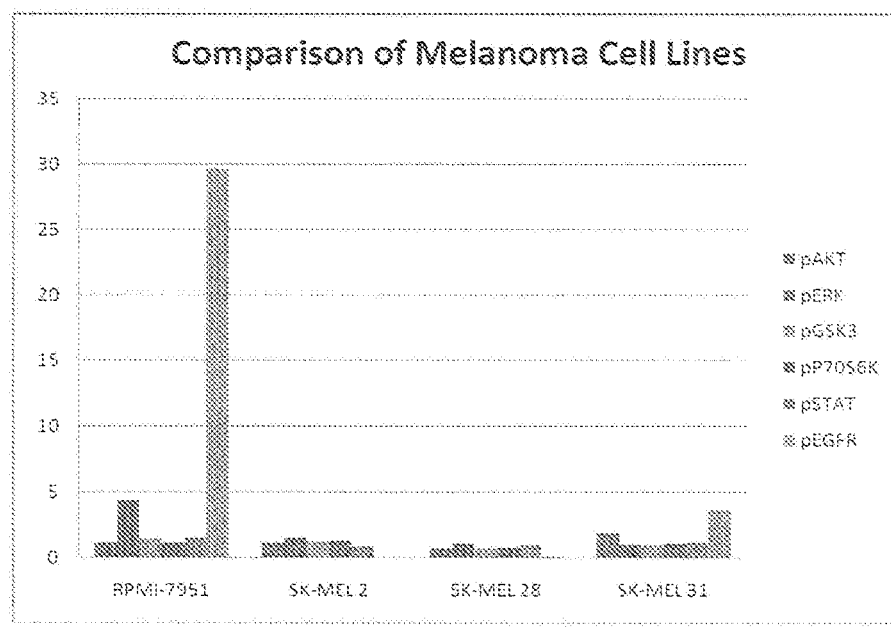
FIG. 15 shows exemplary melanoma functional signaling profiles (modulation) upon EGF stimulation. Protein levels are measured for pAKT, pERK, pGSK3, p70S6K, pSTAT, pEGFR in RPMI-7951, SK-MEL 2, SK-MEL 28, and SK-MEL 31 cells. Fold changes are calculated for protein level before and after EGF stimulation.
Figure 16:
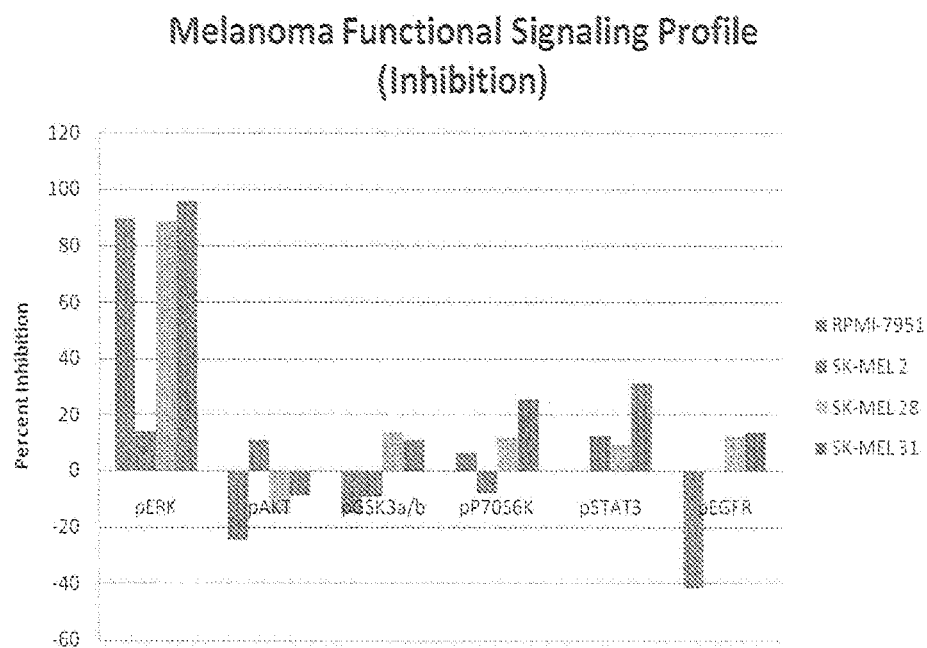
FIG. 16 shows exemplary melanoma functional signaling profiles (inhibition) upon MEK inhibition by U0126. Protein levels are measured for pERK, pAKT, pGSK3α/β, p70S6K, pSTAT, pEGFR in RPMI-7951, SK-MEL 2, SK-MEL 28, and SK-MEL 31 cells.
Figure 17:
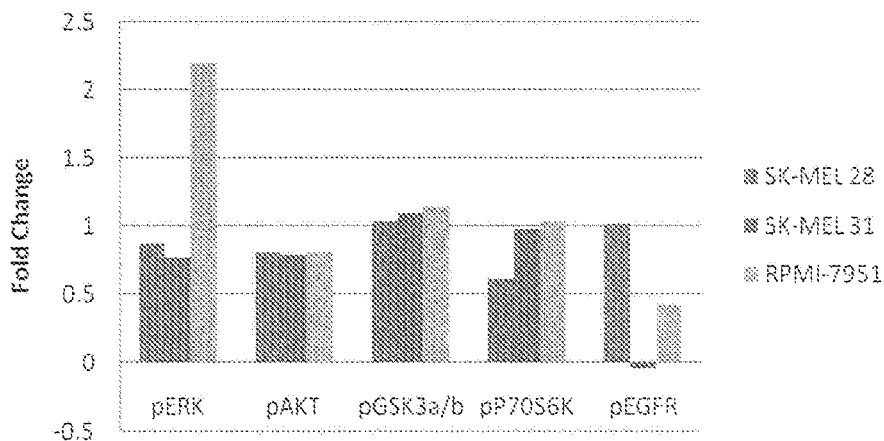
FIG. 17 shows exemplary differentiation of PLX-4032 resistant cell line RPMI-7951 through the induction of pErk following stimulation by TPA.

FIGS. 15-17 and 19-36 also demonstrate several specific examples of functional signaling profile features that distinguish melanoma samples and correlate with drug sensitivity or resistance. For example, FIG. 15 shows that the SK-MEL-31 and RMPI-7951 cell lines display the highest induction of pEGFR upon EGF stimulation. Surprisingly, these two cell lines also display resistance to the BRAF inhibitor PLX-4032. Basal levels of various proteins can also distinguish melanomas. For example, SK-MEL-31, SK-MEL-28, SK-MEL-2 and RPMI-7951 cell lines display different basal levels of pERK (1816, 3880, 1948 and 776 avg. MFI, respectively) and pAKT. Additionally, FIG. 16 shows that MEK inhibition by U0126 also demonstrates unique functional circuitry of each cell line, including unanticipated enhancement of collateral pathways, such as those marked by pERK and pEGFR. FIG. 17 shows differentiation of PLX-4032 resistant cell line RPMI-7951 through the induction of pErk following stimulation by TPA. Additionally, FIGS. 19-34 demonstrate the ability distinguish melanoma cell lines based on modulation with TPA, EGF, PDGFβ, or inhibition with PLX-4702 or U0126.

Figure 19:
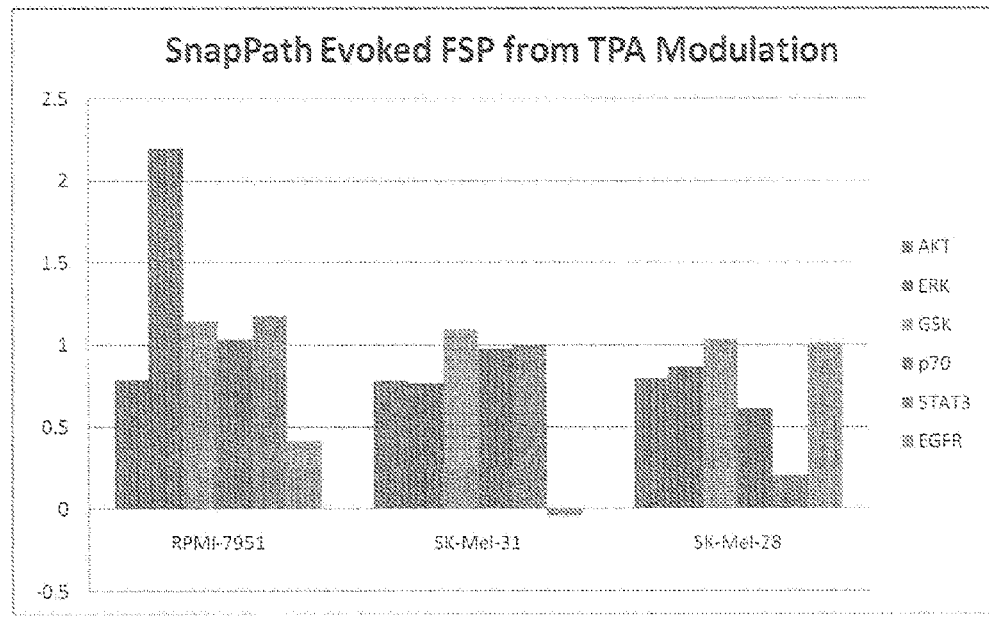
FIG. 19 shows exemplary melanoma cell line functional signaling profiles following stimulation with TPA on the SnapPath™ instrument. Protein levels measured include pAKT, pErk, pGSK3β, pP70S6k, pSTAT3, and pEGFR.
Figure 20:
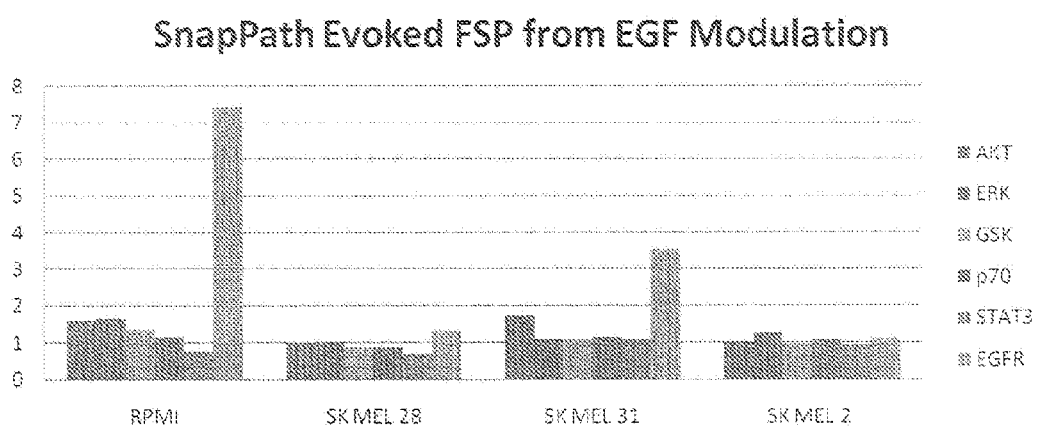
FIG. 20 shows exemplary melanoma cell line functional signaling profiles following stimulation with EGF on the SnapPath™ instrument. Protein levels measured include pAKT, pErk, pGSK3β, pP70S6k, pSTAT3, and pEGFR.

FIGS. 19-36 demonstrate the ability distinguish melanoma cell lines based on modulation with TPA EGF, PDGFβ, or inhibition with PLX-4702 or U0126. For example FIGS. 19 and 20 show evoked functional signaling profiles from four different melanoma cell lines modulated with TPA and EGF. As seen in FIG. 20. RPMI-7951 and SK-MEL-31 have differentiating levels of pEGFR following stimulating with EGF.

Figure 21:
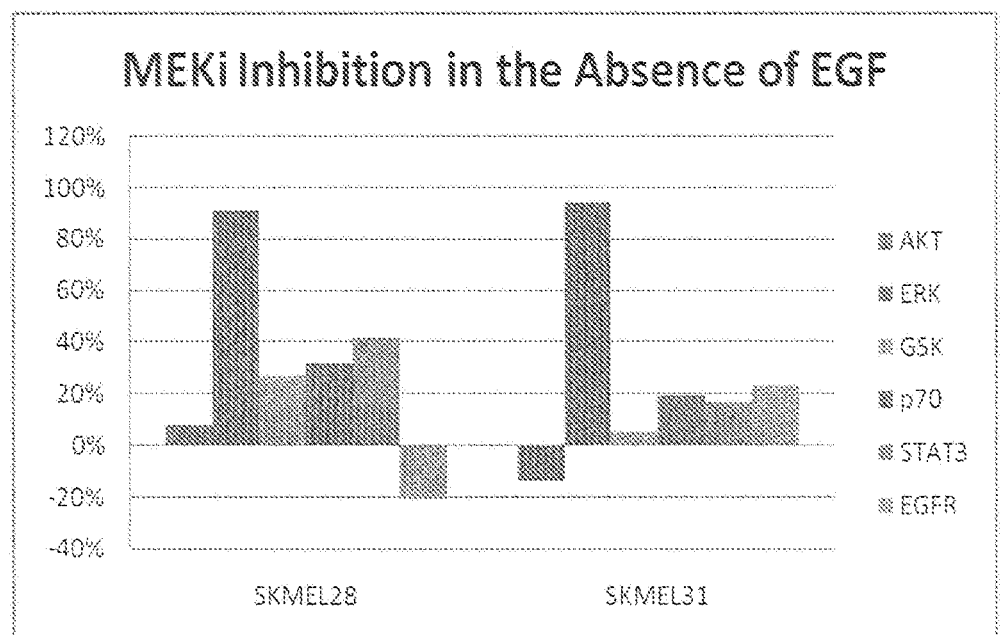
FIG. 21 shows exemplary melanoma cell line functional signaling profiles following inhibition with U0126 in the absence of EGF on the SnapPath™ instrument. Protein levels measured include pAKT, pErk, pGSK3β, pP70S6k, pSTAT3, and pEGFR.
Figure 22:
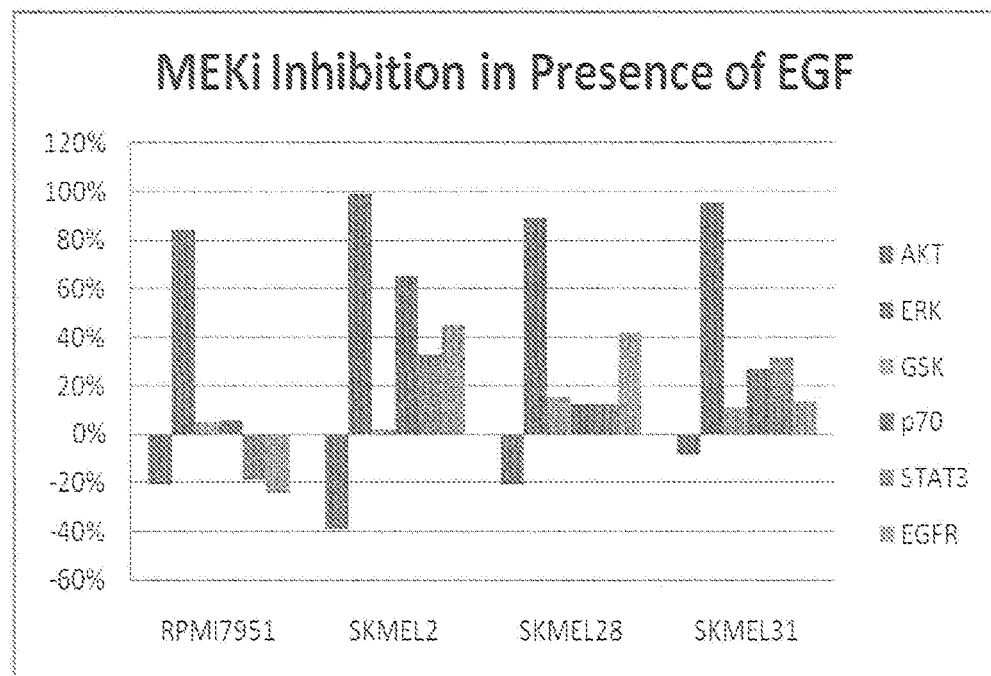
FIG. 22 shows exemplary melanoma cell line functional signaling profiles following inhibition with U0126 in the presence of EGF on the SnapPath™ instrument. Protein levels measured include pAKT, pErk, pGSK3β, pP70S6k, pSTAT3, and pEGFR.

FIGS. 21 and 22 demonstrate the impact of MEK inhibition by U0126 in the absence (FIG. 21) and presence (FIG. 22) of EGF modulation in four melanoma cell lines. In the absence of EGF stimulation and MEK inhibition in SK-MEL-28 cells pErk is inhibited while pEGFR is activated. In SK-MEL-31 cells, pErk is inhibited as well at a comparable level though pAkt is upregulated following inhibition. Comparable trends are also demonstrated in FIG. 22.

Figure 23:
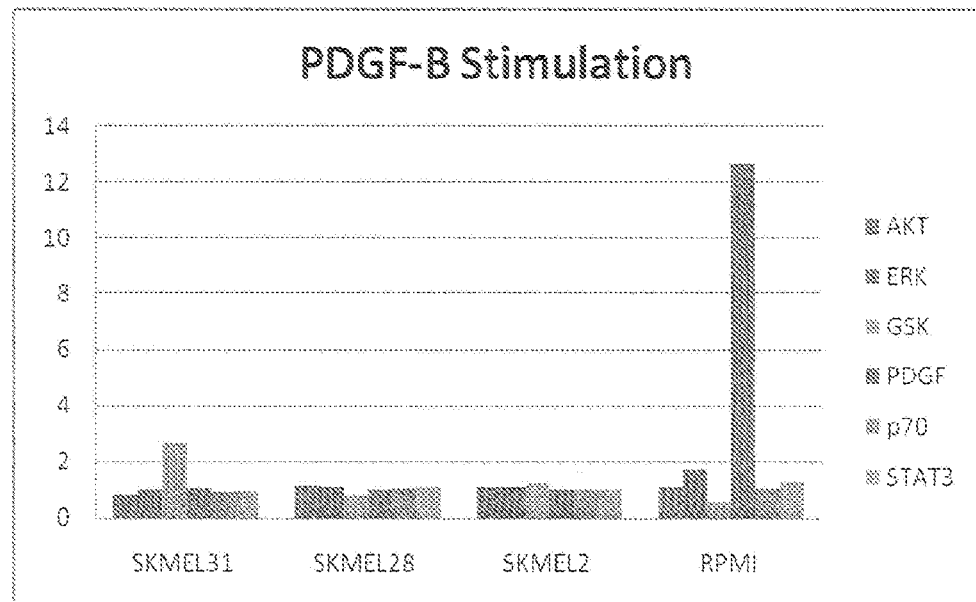
FIG. 23 shows exemplary melanoma cell line functional signaling profiles following stimulation of PDGF-β on the SnapPath™ instrument. Protein levels measured include pAKT, pErk, pGSK3β, pP70S6k, pSTAT3, and pEGFR.
Figure 24:
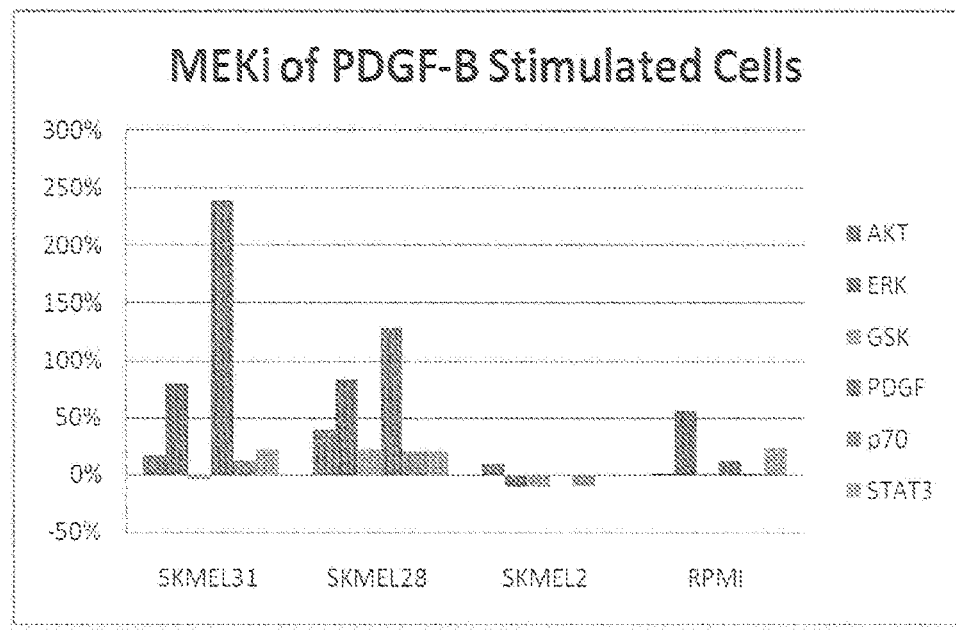
FIG. 24 shows exemplary melanoma cell line functional signaling profiles following stimulation of PDGF-β and MEK inhibition by U0126 on the SnapPath™ instrument. Protein levels measured include pAKT, pErk, pGSK3β, pP70S6k, pSTAT3, and pEGFR.
Figure 25:
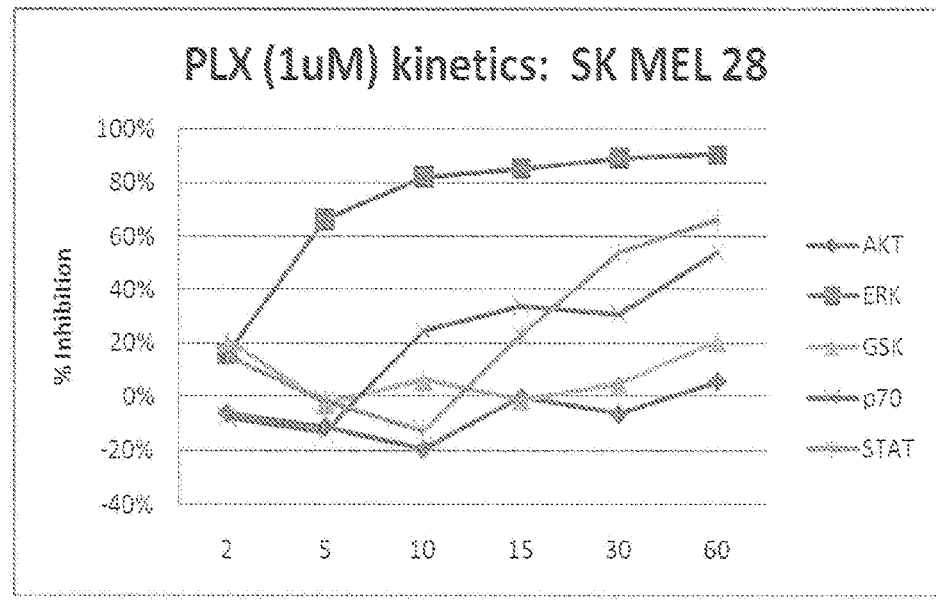
FIG. 25 shows exemplary kinetic curves of phosphoprotein inhibition in SK-MEL-28, a melanoma cell line, following treatment with a BRAF inhibitor (PLX-4702) on the SnapPath™ instrument. Protein levels measured include pAKT, pErk, pGSK3β, pP70S6k, and pSTAT3
Figure 26:
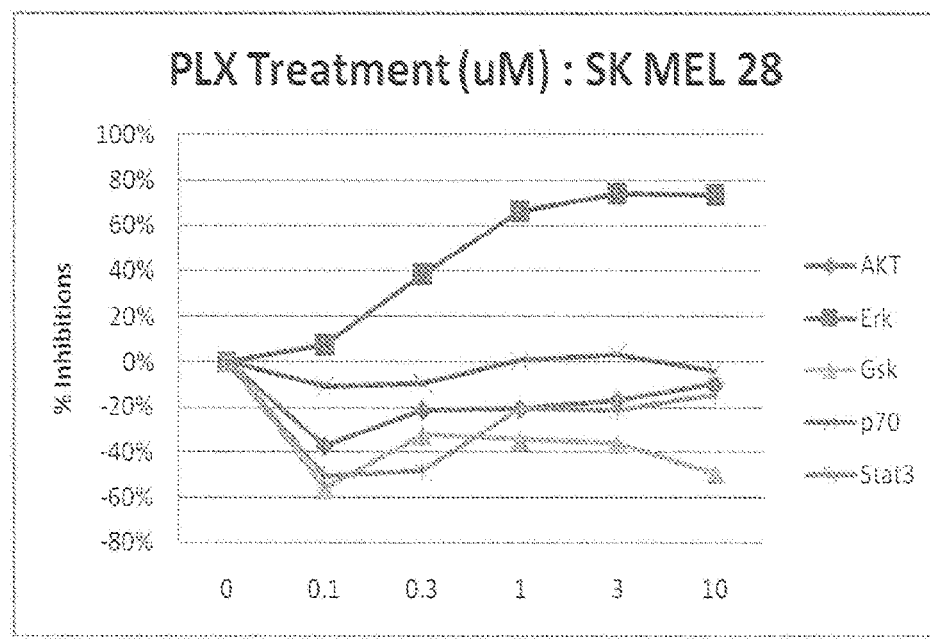
FIG. 26 shows exemplary dose response curves of phosphoprotein inhibition in SK-MEL-28, a melanoma cell line following treatment with a BRAF inhibitor (PLX-4702) on the SnapPath™ instrument. Protein levels measured include pAKT, pErk, pGSK3β, pP70S6k, and pSTAT3.
Figure 27:
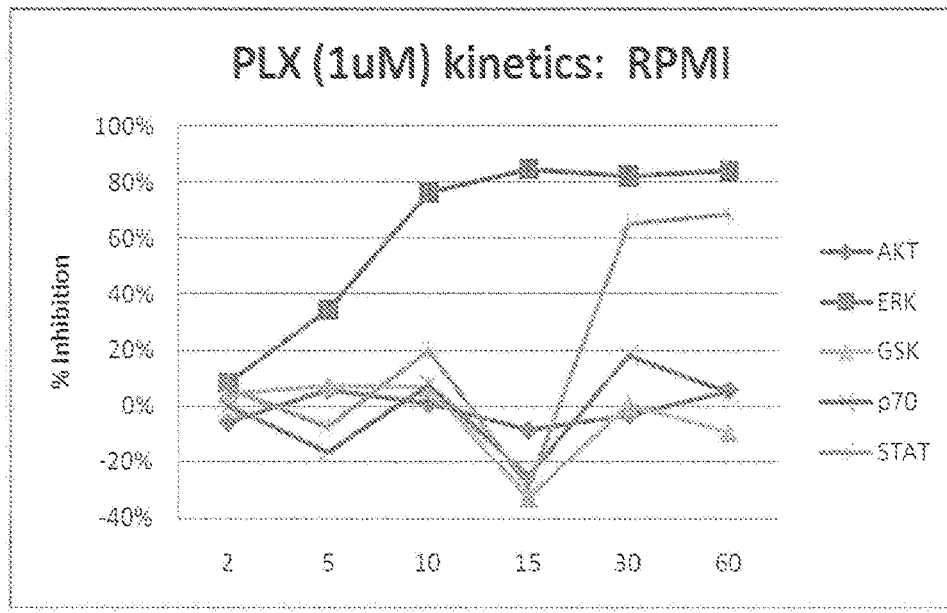
FIG. 27 shows exemplary kinetic curves of phosphoprotein inhibition in RPMI-7951, a melanoma cell line, following treatment with a BRAF inhibitor (PLX-4702) on the SnapPath™ instrument. Protein levels measured include pAKT, pErk, pGSK3β, pP70S6k, and pSTAT3
Figure 28:
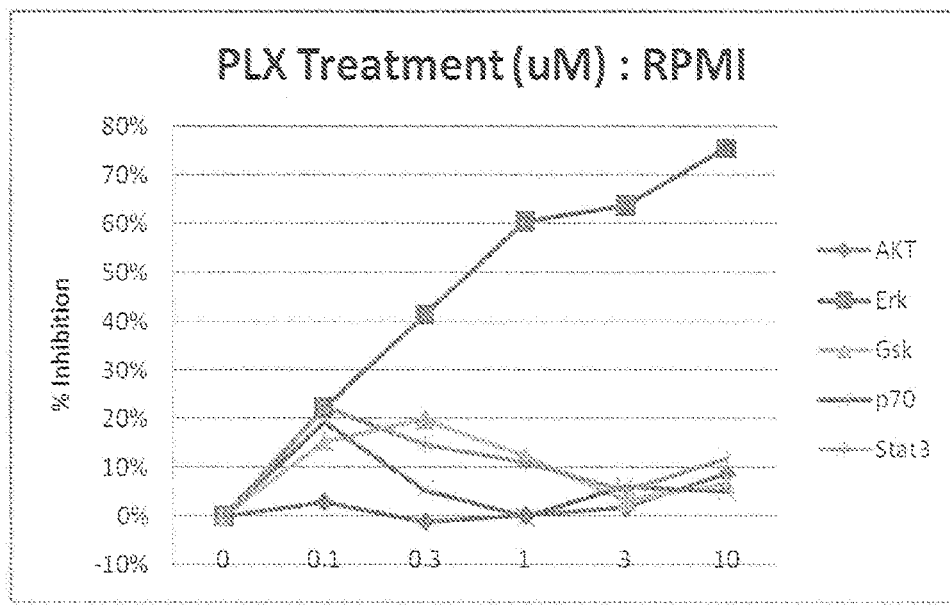
FIG. 28 shows exemplary dose response curves of phosphoprotein inhibition in RPMI-7951, a melanoma cell line, following treatment with a BRAF inhibitor (PLX-4702) on the SnapPath™ instrument. Protein levels measured include pAKT, pErk, pGSK3β, pP70S6k, and pSTAT3.
Figure 29:
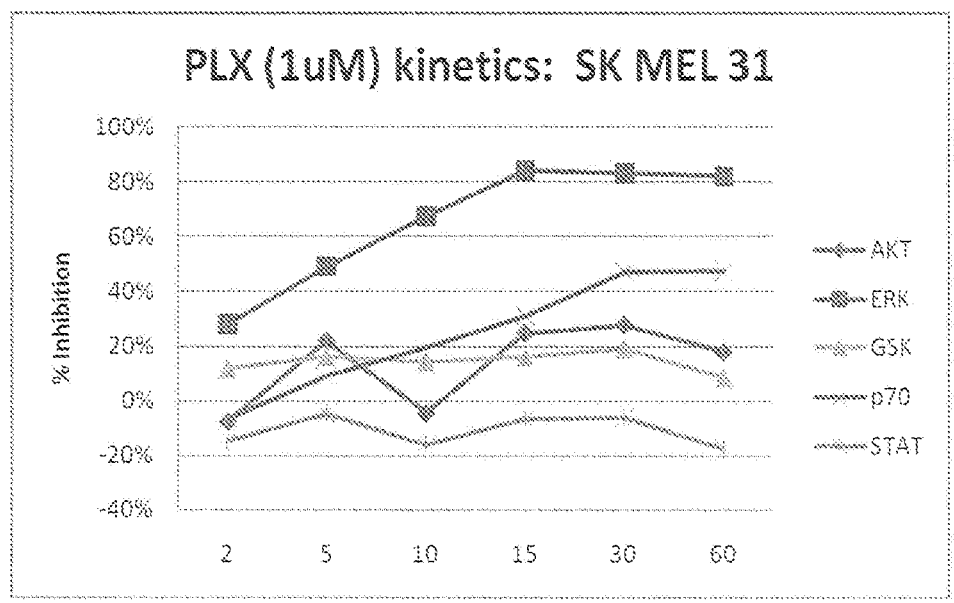
FIG. 29 shows exemplary kinetic curves of phosphoprotein inhibition in SK-MEL-31, a melanoma cell line, following treatment with a BRAF inhibitor (PLX-4702) on the SnapPath™ instrument. Protein levels measured include pAKT, pErk, pGSK3β, pP70S6k, and pSTAT3
Figure 30:
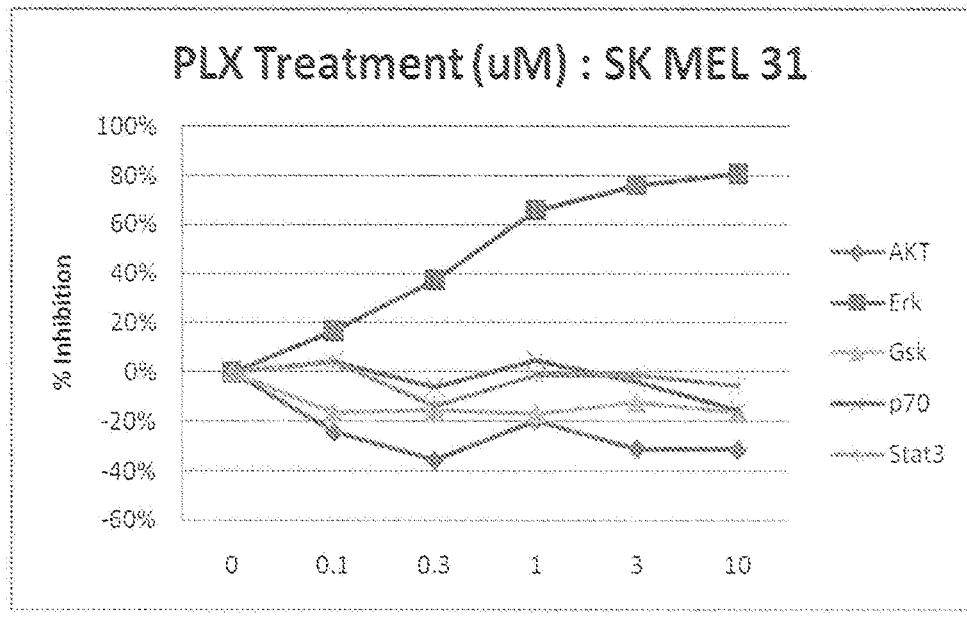
FIG. 30 shows exemplary dose response curves of phosphoprotein inhibition in SK-MEL-31, a melanoma cell line, following treatment with a BRAF inhibitor (PLX-4702) on the SnapPath™ instrument. Protein levels measured include pAKT, pErk, pGSK3β, pP70S6k, and pSTAT3.
Figure 31:
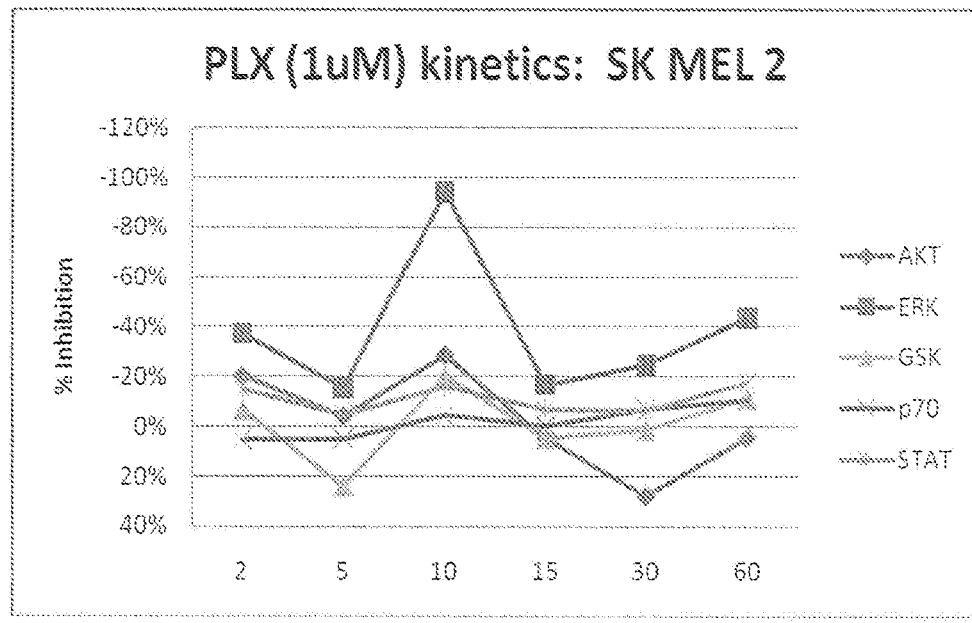
FIG. 31 shows exemplary kinetic curves of phosphoprotein inhibition in SK-MEL-2, a melanoma cell line, following treatment with a BRAF inhibitor (PLX-4702) on the SnapPath™ instrument. Protein levels measured include pAk, pErk, pGSK3β, pP70S6k, and pSTAT3
Figure 32:
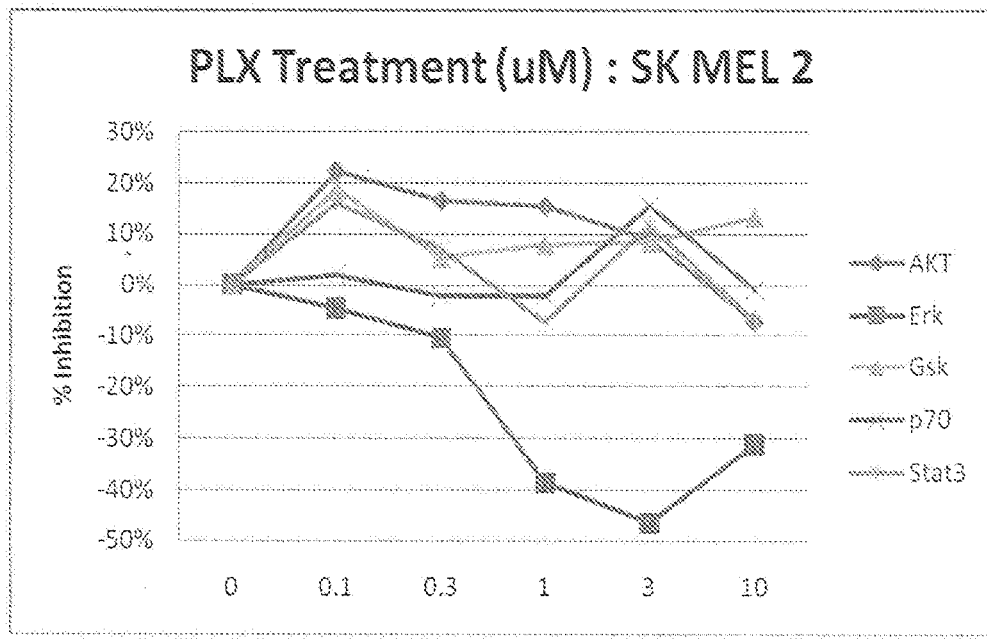
FIG. 32 shows exemplary dose response curves of phosphoprotein inhibition in SK-MEL-2, a melanoma cell line, following treatment with a BRAF inhibitor (PLX-4702) on the SnapPath™ instrument. Protein levels measured include pAKT, pErk, pGSK3β, pP70S6k, and pSTAT3.

FIGS. 23 and 24 demonstrate the impact of PDGFβ stimulation on melanoma cell lines as well as MEK inhibition of PDGFβ stimulation. PDGFβ stimulation activated pPDGF in RPMI-7951 cell lines uniquely compared to other melanoma cell lines. MEK inhibition reduces pErk by approximately 50% in SK-MEL-21, SK-MEL-28 and RPMI-7951 cell lines. pErk is not impacted by MEK inhibition in SK-MEL-2 cell lines.

Figure 33:
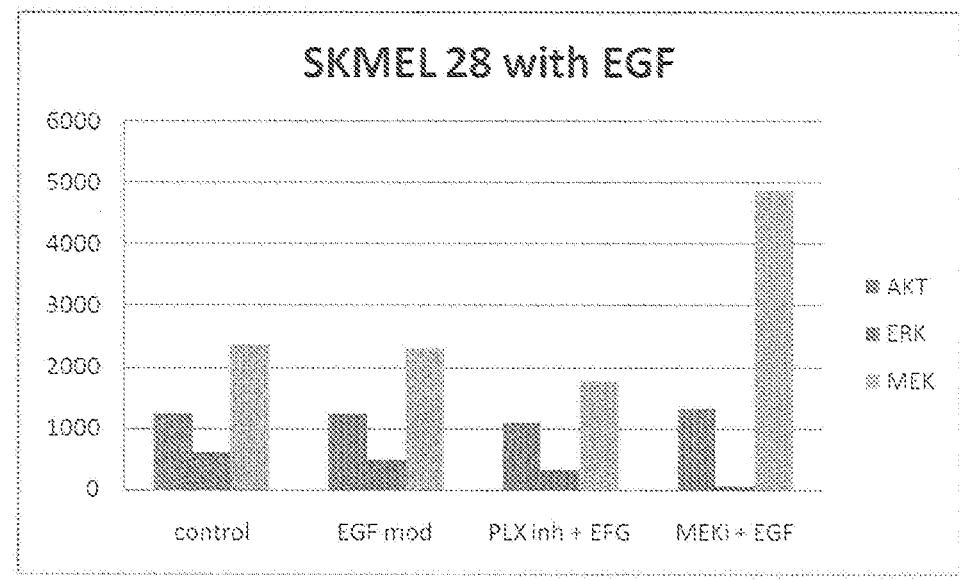
FIG. 33 shows exemplary melanoma cell line (SK-MEL-28) functional signaling profiles following stimulation of EGF on the SnapPath™ instrument. Protein levels measured include pAKT, pErk, pMEK.
Figure 34:
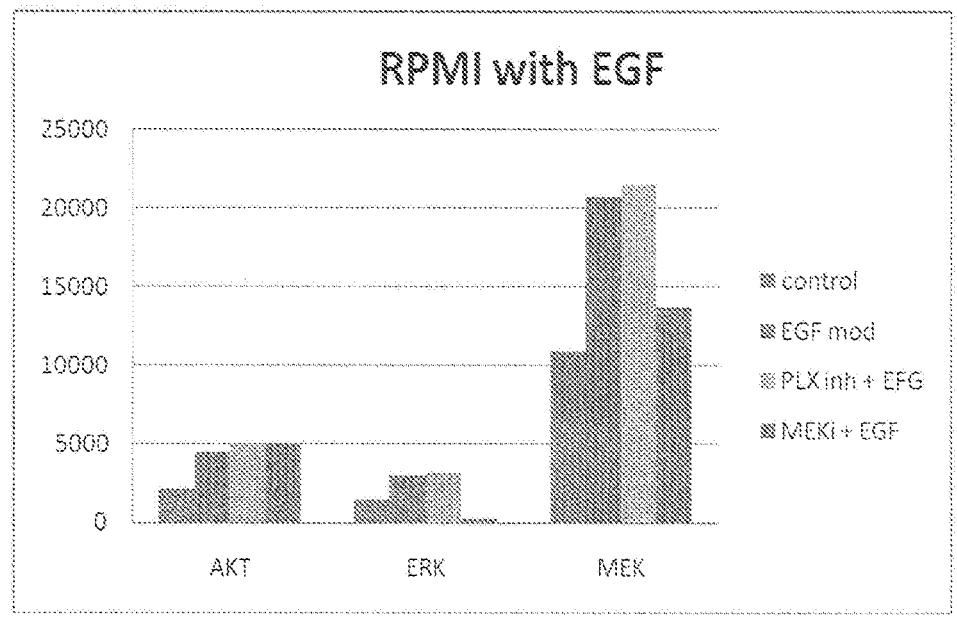
FIG. 34 shows exemplary melanoma cell line (RPMI-7951) functional signaling profiles following stimulation of EGF as well as BRAF and ERK inhibition with PLX-4702 and U0126 on the SnapPath™ instrument. Protein levels measured include pAKT, pErk, pMEK.

FIGS. 33 and 34 demonstrate the impact of EGF stimulation on SK-MEL-28 cell lines in the presence of BRAF inhibitor PLX-4702 and MEK inhibitor U0126. PLX inhibition plus EGF stimulation reduced pERk expression though not as significantly as MEK inhibition. pMEK was also increased in the presence of the MEK inhibitor and EGF.

Figure 35:
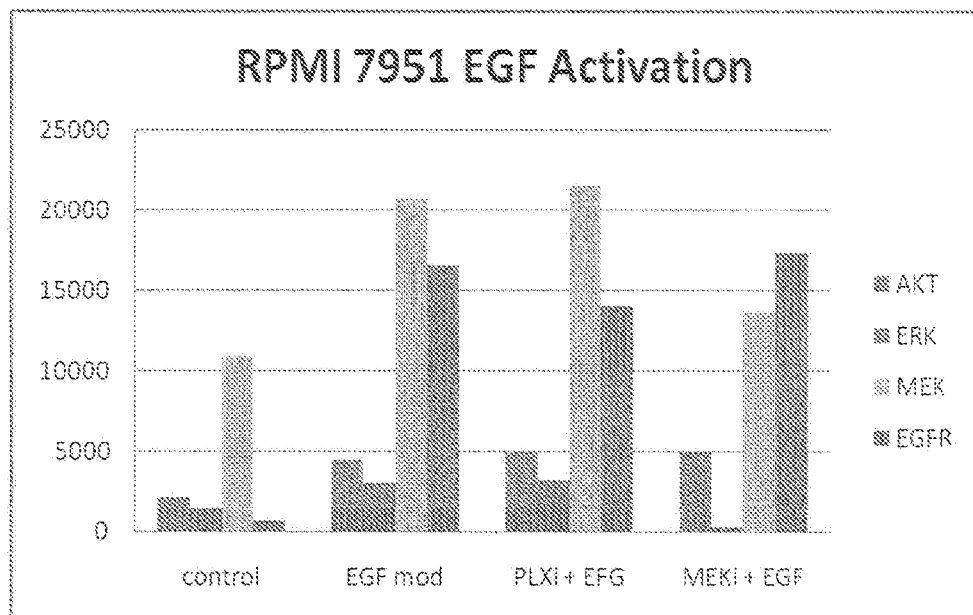
FIG. 35 shows exemplary melanoma cell line (RPMI-7951) functional signaling profiles following stimulation of EGF as well as BRAF and ERK inhibition with PLX-4702 and U0126 on the SnapPath™ instrument. Protein levels measured include pAKT, pErk, pMEK and pEGFR.

FIG. 35 demonstrates the impact of EGF stimulation and PLX-4072 or MEK inhibition in RPMI-7951 cells. pEGFR is dramatically increased follow all EGF modulation while pErk is decreased following MEK inhibition.

Figure 36:
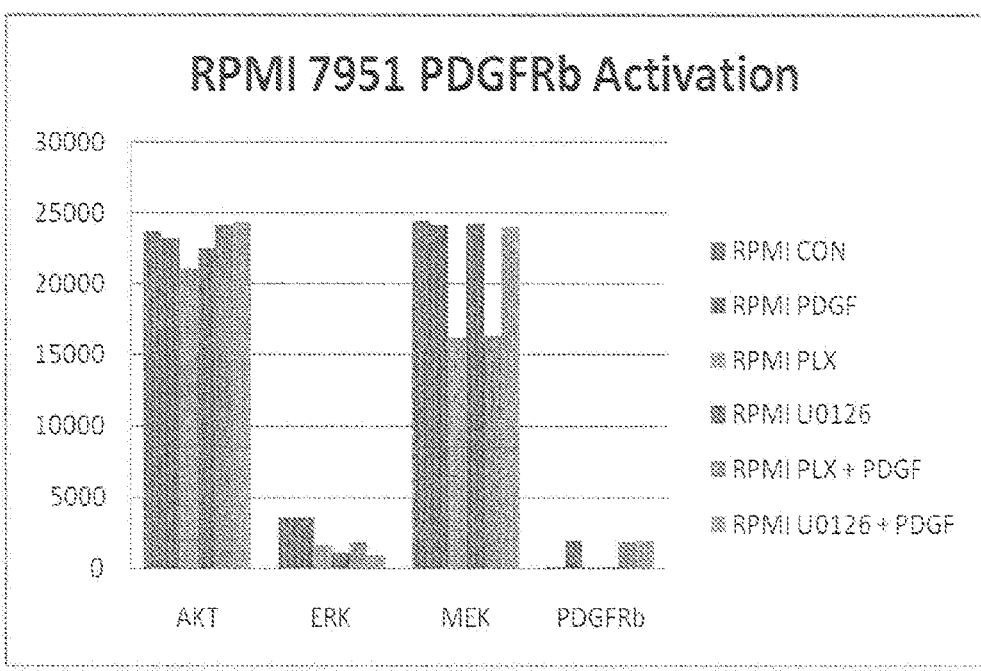
FIG. 36 shows exemplary melanoma cell line (RPMI-7951) functional signaling profiles following stimulation of PDGFβ as well as BRAF and ERK inhibition with PLX-4702 and U0126 on the SnapPath™ instrument. Protein levels measured include pAKT, pErk, pMEK.

FIG. 36 demonstrates PDGFRβ activation of RPMI-7951 cell in the absence or presence of MEK inhibitor, U0126, or BRAF inhibitor, PLX-4702. pMEK is down-regulated in the presence of PLX-4702, while MEK inhibition appears less effective.

Example 5

Functional Signaling Profiles of Pancreas Cancer Cells

Pancreatic neuroendocrine tumors (PancNETs) are the second most common tumor of the pancreas, although they most likely represent a heterogeneous group of related tumors. The malignant potential of PancNETs varies widely and cannot be predicted based on microscopic analysis or standard immunohistochemical tests, such as those for proliferation rates. Functional signaling profiles offer an opportunity to identify tumors with worse prognosis, as well as the possibility of identifying molecular features that would enable the prediction of appropriate targeted therapy.

Figure 18:
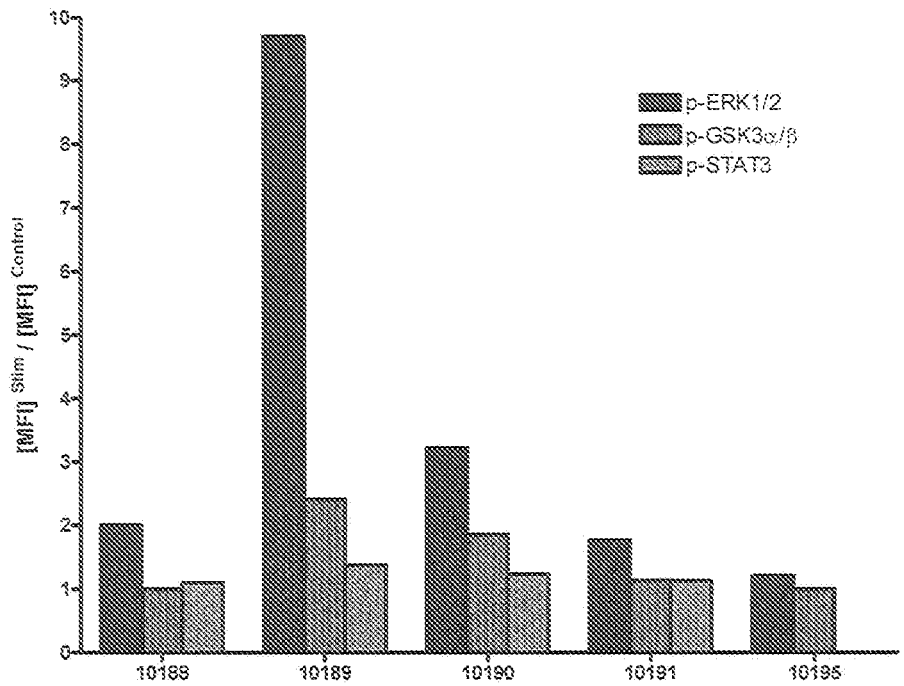
FIG. 18 shows exemplary pancreatic tumor functional signaling profiles. All samples except 10195 are examples of human pancreatic neuroendocrine tumors (PanNETs). 10195 is a sample of a human pancreatic adenocarcinoma. The data reveal differences in functional profiles based on TPA stimulation using three different phosphoprotein biomarkers (p-ERK1/2, p-GSKα/β, and p-STAT3).

As shown in FIG. 18, functional signaling profiles can distinguish and stratify pancreatic tumor samples based on differences in their signal transduction circuitry. Such profiles can be generated by comparing basal levels of various proteins (including pErk, pAKT, pP70S6k, pGSK3β, pEGFR and pSTAT3) to levels upon exposure of cells to various agents (including EGF, TPA, other growth factors, etc.). In addition, perturbing signal transduction networks by exposing the melanoma cells to various agents (such as MEK inhibitors, mTOR inhibitors, etc.) can reveal additional functional information, including the elucidation of drug resistance mechanisms and oncogene bypass mechanisms. Taken together, such functional signaling profiles can form the foundation for prognostic, predictive, pharmacodynamic, or monitoring tests.

FIG. 18 also shows several functional signaling profile features that distinguish pancreatic tumor samples and correlate with drug sensitivity or resistance. These studies utilized actual human tumor samples from individuals with pancreatic neuroendocrine tumors or pancreatic adenocarcinoma. For example, FIG. 18 shows that the four PancNETs can be distinguished by their functional profiles as determined by induction of pERK and pGSK upon TPA stimulation. Surprisingly, the sample with the most distinctive functional profile (10189; 10× pERK induction) was the only tumor that was metastatic. This suggests that such a functional profile can provide prognostic information about pancreatic tumors. Basal levels of various proteins can also distinguish pancreatic tumors. Functional profiles based on perturbation by agents such as drugs, including mTOR inhibitors, provide additional information, some of which can form the basis for predictive tests.

Although the invention has been described with reference to the above examples, it will be understood that modifications and variations are encompassed within the spirit and scope of the invention. Accordingly, the invention is limited only by the following claims.

What is claimed is:

1. A method of determining the difference between a basal level or state of a class of proteins in a cell sample and the level or state of the proteins after contacting with a modulator comprising: contacting a first portion of the sample with a modulator ex vivo within a cartridge to evoke functional signaling profiles not found in the cells in vivo prior to contacting with the modulator, and contacting a second portion of the sample with a control ex vivo within the cartridge prior to, simultaneously with or following a therapeutic agent, therapeutic regimen, or course of therapy; wherein determining the difference is by using a computer, wherein the difference in the basal level or state of the proteins is expressed as a value by the computer and is used to create functional signaling profiles that stratify the samples into functional groups, wherein the protein is a protein post-translationally modified by a kinase, a phosphatase, or a proteolytic enzyme; and wherein the modulator is a MBK inhibitor, mTor inhibitor, EGF receptor inhibitor, BRAF inhibitor or a combination thereof.

2. The method of claim 1, wherein the sample is selected from the group consisting of tissue, blood, ascites, saliva, urine, perspiration, tears, semen, serum, plasma, amniotic fluid, pleural fluid, cerebrospinal fluid, a cell line, a xenograft, a tumor, pericardial fluid, and combinations thereof.

3. The method of claim 2, wherein the tumor sample is from a solid tumor.

4. The method of claim 2, wherein the tumor sample is obtained by fine needle aspiration, core biopsy, circulating tumor cells, or surgically excised tissue sample.

5. The method of claim 1, wherein the protein is analyzed using a method selected from the group consisting of an array, ELISA, bioplex, luminex, mass spectrometry, flow cytometry, and RIA.

6. The method of claim 1, wherein the protein activates or inhibits a cellular pathway selected from the group consisting of a metabolic pathway, a replication pathway, a cellular signaling pathway, an oncogenic signaling pathway, an apoptotic pathway, and a pro-angiogenic pathway.

7. The method of claim 1, wherein the protein is selected from the group consisting of p-Erk 1/2, p-AKT, p-EGFR, p-Stat3, pP70S6K, and pGSK3β.

8. The method of claim 1, wherein at least two different groups of functional signaling profiles are identified.

* * * * *